(12) United States Patent
Kajikawa et al.

(10) Patent No.: US 7,910,749 B2
(45) Date of Patent: Mar. 22, 2011

(54) METHODS FOR OXIDIZING ORGANIC COMPOUNDS

(75) Inventors: Yasuteru Kajikawa, Himeji (JP); Naruhisa Hirai, Himeji (JP); Jun Kuwana, Himeji (JP)

(73) Assignee: Daicel Chemical Industrial, Ltd., Sakai-Shi, Osaka (JP)

( * ) Notice: Subject to any disclaimer, the term of this patent is extended or adjusted under 35 U.S.C. 154(b) by 603 days.

(21) Appl. No.: 11/884,203

(22) PCT Filed: Feb. 22, 2006

(86) PCT No.: PCT/JP2006/303139
§ 371 (c)(1),
(2), (4) Date: Aug. 13, 2007

(87) PCT Pub. No.: WO2006/095568
PCT Pub. Date: Sep. 14, 2006

(65) Prior Publication Data
US 2008/0269507 A1 Oct. 30, 2008

(30) Foreign Application Priority Data
Mar. 7, 2005 (JP) .................. 2005-063127

(51) Int. Cl.
| | |
|---|---|
| C07D 493/00 | (2006.01) |
| C07D 307/77 | (2006.01) |
| C07C 61/00 | (2006.01) |
| C07C 51/255 | (2006.01) |
| C07C 45/00 | (2006.01) |
| C07C 27/00 | (2006.01) |
| C07C 35/08 | (2006.01) |
| C07C 35/06 | (2006.01) |

(52) U.S. Cl. ........ 549/239; 549/240; 549/245; 562/400; 562/408; 568/338; 568/700; 568/822; 568/838

(58) Field of Classification Search .................. 549/239, 549/240, 245; 562/400, 408; 568/338, 700, 568/822, 838
See application file for complete search history.

(56) References Cited

U.S. PATENT DOCUMENTS
7,115,541 B2 * 10/2006 Ishii et al. ..................... 502/167
2002/0169331 A1 11/2002 Miura et al.

FOREIGN PATENT DOCUMENTS
EP 1 151 791 A1 11/2001
(Continued)

OTHER PUBLICATIONS
Extended European Search Report for Application No. 06714279.4 dated May 7, 2010 (5 pages).

*Primary Examiner* — Taylor Victor Oh
(74) *Attorney, Agent, or Firm* — Birch, Stewart, Kolasch & Birch, LLP

(57) ABSTRACT

A method oxidizes an organic compound with oxygen in the presence of a catalyst, in which the catalyst contains a N-hydroxy- or N-(substituted oxy)-imide compound derivable from at least one selected from a target product, a reaction intermediate, and a reaction byproduct, and the catalyst is produced from at least one component selected from the target product, reaction intermediate, and reaction byproduct each formed as a result of the reaction and is used in the oxidation reaction so as to make up for a loss of the catalyst due to denaturation in the reaction. The method can easily and inexpensively make up for a loss of the catalyst denaturated in the course of reaction.

13 Claims, 1 Drawing Sheet

FOREIGN PATENT DOCUMENTS

| | | |
|---|---|---|
| JP | 8-38909 A | 2/1996 |
| JP | 9-327626 | 12/1997 |
| JP | 10-57814 A | 3/1998 |
| JP | 11-188265 A | 7/1999 |
| JP | 2001-286765 A | 10/2001 |
| JP | 2001-288122 A | 10/2001 |

* cited by examiner

METHODS FOR OXIDIZING ORGANIC COMPOUNDS

TECHNICAL FIELD

The present invention relates to oxidation methods of organic compounds, and production processes of organic compounds. More specifically, it relates to oxidation methods and production processes of organic compounds by the catalysis of imide compounds, which can reduce cost for making up for losses of the catalysts denaturated in the reaction.

BACKGROUND ART

Imide compounds such as N-hydroxyimide compounds, N-alkoxyimide compounds, and N-acyloxyimide compounds are known to act as very excellent catalysts in oxidation of organic compounds using molecular oxygen, since they show high reaction efficiencies and high selectivities and can be applied to a wide variety of substrates in the oxidation (e.g., Patent Documents 1, 2 and 3). However, these imide compounds undergo denaturation and thereby gradually decrease in activity in reaction. The denaturation may occur through several processes, and main possible factors thereof are as follows.

The imide compounds change into N-hydroxyimides before they develop activities in the reaction. A possible mechanism for developing the activity is as follows. Initially, oxygen atom and hydrogen atom of the hydroxyl group adjacent to the nitrogen atom of imide easily undergo homogenous dissociation to form a radical. The formed radical withdraws hydrogen from a substrate to be oxidized to initiate a radical chain of oxidation reaction. The catalyst imide compound returns to its original configuration, repeats the same operation, and elongates the radical chain. However, the radical formed from the N-hydroxyimide inevitably induces, due to its own nature, a "termination reaction" in which the radical is bound typically to a radical formed from the substrate to be oxidized. As a result, the N-hydroxyimide structure serving as an active site of the N-hydroxyimide is lost. The resulting compound derived from N-hydroxyimide and formed in the termination reaction further undergoes denaturation without returning to the N-hydroxyimide.

In another possible denaturation process, the imide moieties of imide compounds may be hydrolyzed by water formed in oxidation reactions and thereby undergo denaturation. In yet another possible denaturation process, N—O bond (nitrogen-oxygen bond) of imide compounds may be cleaved typically by the action of a coexistent metal promoter (co-catalyst). In any case, when the imide compounds are reused, losses thereof due to denaturation in the course of reaction must be made up for regardless of the reaction system such as batch system or continuous system, and this invites increased cost.

As possible solutions to these problems, Patent Documents 4 and 5 each disclose a technique of recovering a denatured product (decomposed product) of a N-hydroxyimide compound, subjecting the same to a certain treatment according to necessity, reacting the treated product with hydroxylamine to reconstruct a N-hydroxyimide structure as an active site to thereby regenerate the N-hydroxyimide compound, and using the regenerated compound in oxidation. This technique is economically advantageous as compared with the cases where a fresh N-hydroxyimide compound is purchased or the compound is produced after purchasing materials for the compound. However, isolation of denaturated N-hydroxyimide compounds requires much energy, since the amounts of such N-hydroxyimide compounds used in oxidation of organic compounds with molecular oxygen are generally very small. Additionally, it is difficult to fully make up for losses due to denaturation by regenerating the catalysts from the isolated N-hydroxyimide compounds.

Patent Document 1: Japanese Unexamined Patent Application Publication (JP-A) No. 08-38909,
Patent Document 2: Japanese Unexamined Patent Application Publication (JP-A) No. 10-57814,
Patent Document 3: Japanese Unexamined Patent Application Publication (JP-A) No. 09-327626,
Patent Document 4: Japanese Unexamined Patent Application Publication (JP-A) No. 11-188265,
Patent Document 5: Japanese Unexamined Patent Application Publication (JP-A) No. 2001-286765.

DISCLOSURE OF INVENTION

Problems to be Solved by the Invention

Accordingly, an object of the present invention is to provide a method for oxidizing an organic compound and a process for producing an organic compound, which can easily, conveniently, and inexpensively make up for a loss of a catalyst denaturated in the course of an oxidation reaction of an organic compound with oxygen in the presence of a catalyst containing a N-hydroxyimide compound or N-(substituted oxy)-imide compound (a compound having a substituent on oxygen atom bound to the nitrogen atom of imide).

Means for Solving the Problems

After intensive investigations to achieve the object, the present inventors have found that the loss of a catalyst can be easily, conveniently, and inexpensively made up for by using, as the catalyst, one derivable from a reaction product, a reaction intermediate and/or a reaction byproduct, producing the catalyst using the target product, reaction intermediate and/or reaction byproduct, and supplying the produced catalyst to the reaction system, so as to makeup for a loss of the catalyst denaturated in the course of reaction. The present invention has been achieved based on these findings.

Specifically, the present invention provides a method for oxidizing an organic compound with oxygen in the presence of a catalyst, in which the catalyst contains at least one N-hydroxy- or N-(substituted oxy)-imide compound derivable from at least one selected from the group consisting of a target product, a reaction intermediate, and a reaction byproduct, and the method includes the steps of producing the catalyst from at least one component selected from the group consisting of the target product, reaction intermediate, and reaction byproduct each formed as a result of the reaction, and using the produced catalyst in the oxidation reaction so as to make up for a loss of the catalyst due to denaturation in the reaction. Cyclic N-hydroxy- or N-(substituted oxy)-imide compounds are preferred as the N-hydroxy- or N-(substituted oxy)-imide compound.

In the oxidation method, an undenaturated catalyst can be recovered from the reaction mixture and used in the oxidation reaction, in addition to the catalyst produced from at least one component selected from the group consisting of a target product, a reaction intermediate, and a reaction byproduct each formed as a result of the reaction. The at least one component selected from the group consisting of the target product, reaction intermediate, and reaction byproduct is preferably at least one of polycarboxylic acids, polycarboxylic acid anhydrides, and mixtures of them.

The oxidation method of an organic compound according to the present invention can be a method for oxidizing a cycloalkane represented by following Formula (1):
[Chemical Formula 1]

(1)

wherein "n" represents an integer of 4 to 20, and the ring shown in the formula may be substituted, with oxygen to thereby yield at least one selected from the group consisting of corresponding cycloalkanones, corresponding cycloalkanols, and corresponding dicarboxylic acids having carbon atoms in the number of "n" in principal chain, in which the catalyst contains at least one cyclic N-hydroxy- or N-(substituted oxy)-imide compound derivable from at least one selected from the group consisting of a target product, a reaction intermediate, and a reaction byproduct and represented by following Formula (2):
[Chemical Formula 2]

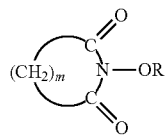

(2)

wherein "m" represents an integer of 2 to (n−2); and R represents hydrogen atom or an organic group, and wherein the ring shown in the formula may be substituted, and the method includes the steps of producing the catalyst from at least one component selected from the group consisting of the target product, reaction intermediate, and reaction byproduct each formed as a result of the reaction, and using the produced catalyst in the oxidation reaction so as to make up for a loss of the catalyst due to denaturation in the reaction.

The method just mentioned above includes, for example, (i) an embodiment for oxidizing cyclohexane with oxygen to thereby yield at least one selected from the group consisting of cyclohexanone, cyclohexanol, and adipic acid, in which the catalyst contains at least one selected from the group consisting of N-hydroxy- or N-(substituted oxy)-succinimide and N-hydroxy- or N-(substituted oxy)-glutarimide derived from succinic acid and glutaric acid, respectively, each as a reaction byproduct, and the method includes the steps of producing the catalyst from succinic acid and/or glutaric acid formed as a result of the reaction, and using the produced catalyst in the oxidation reaction so as make up for a loss of the catalyst due to denaturation in the reaction; (ii) an embodiment for oxidizing cyclopentane with oxygen to thereby yield at least one selected from the group consisting of cyclopentanone, cyclopentanol, and glutaric acid, in which the catalyst contains at least one selected from the group consisting of N-hydroxy- or N-(substituted oxy)-succinimide derived from succinic acid as a reaction byproduct, and N-hydroxy- or N-(substituted oxy)-glutarimide derived from glutaric acid as a target product, and the method includes the steps of producing the catalyst from succinic acid and/or glutaric acid formed as a result of the reaction, and using the produced catalyst in the oxidation reaction so as make up for a loss of the catalyst due to denaturation in the reaction; and (iii) an embodiment for oxidizing cyclododecane with oxygen to thereby yield at least one selected from the group consisting of cyclododecanone, cyclododecanol, and dodecanedioic acid, in which the catalyst includes at least one selected from the group consisting of N-hydroxy- or N-(substituted oxy)-succinimide, and N-hydroxy- or N-(substituted oxy)-glutarimide derived from succinic acid and glutaric acid, respectively, as reaction byproducts, and the method includes the steps of producing the catalyst from succinic acid and/or glutaric acid formed as a result of the reaction, and using the produced catalyst in the oxidation reaction so as make up for a loss of the catalyst due to denaturation in the reaction.

The oxidation method of an organic compound according to the present invention can be a method for oxidizing a compound represented by following Formula (3):
[Chemical Formula 3]

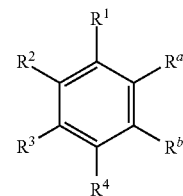

(3)

wherein $R^a$ and $R^b$ are the same as or different from each other and each represent a group convertible into carboxyl group upon oxidation; $R^1$, $R^2$, $R^3$, and $R^4$ are the same as or different from one another and each represent hydrogen atom, a halogen atom, or an organic group, where two or more of $R^a$, $R^b$, $R^1$, $R^2$, $R^3$, and $R^4$ may be combined to form an aromatic or nonaromatic ring together with one or more carbon atoms constituting the benzene ring, with oxygen to thereby yield at least one selected from the group consisting of an aromatic dicarboxylic acid represented by following Formula (4a) and an aromatic dicarboxylic acid anhydride represented by following Formula (4b):
[Chemical Formula 4]

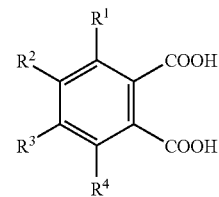

(4a)

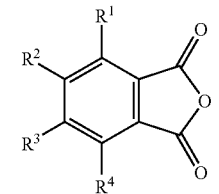

(4b)

wherein $R^1$, $R^2$, $R^3$, and $R^4$ are the same as or different from one another and each represent hydrogen atom, a halogen atom, or an organic group, where two or more of $R^1$, $R^2$, $R^3$, and $R^4$ may be combined to form an aromatic or nonaromatic ring together with one or more carbon atoms constituting the benzene ring, in which the catalyst contains at least one cyclic imide compound derivable from at least one selected from the group consisting of the target product, a reaction intermediate, and a reaction byproduct and represented by following Formula (5):

[Chemical Formula 5]

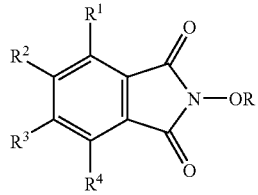

(5)

wherein $R^1$, $R^2$, $R^3$, and $R^4$ are the same as or different from one another and each represent hydrogen atom, a halogen atom, or an organic group, where two or more of $R^1$, $R^2$, $R^3$, and $R^4$ may be combined to form an aromatic or nonaromatic ring together with one or more carbon atoms constituting the benzene ring; and R represents hydrogen atom or an organic group, and the method includes the steps of producing the catalyst from at least one component selected from the group consisting of the target product, reaction intermediate, and reaction byproduct each formed as a result of the reaction, and using the produced catalyst in the oxidation reaction so as to make up for a loss of the catalyst due to denaturation in the reaction. In this case, the catalyst can be produced from at least one component selected from the group consisting of the aromatic dicarboxylic acid represented by Formula (4a) and the aromatic dicarboxylic acid anhydride represented by Formula (4b) each formed as a result of the reaction and the produced catalyst can be used in the oxidation reaction.

The oxidation method of an organic compound according to the present invention can be a method for oxidizing a compound represented by following Formula (6):

[Chemical Formula 6]

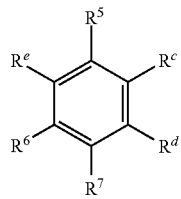

(6)

wherein $R^c$, $R^d$, and $R^e$ are the same as or different from one another and each represent a group convertible into carboxyl group upon oxidation; and $R^5$, $R^6$, and $R^7$ are the same as or different from one another and each represent hydrogen atom, a halogen atom, or an organic group, where two or more of $R^c$, $R^d$, $R^e$, $R^5$, $R^6$, and $R^7$ may be combined to form an aromatic or nonaromatic ring together with one or more carbon atoms constituting the benzene ring, with oxygen to thereby yield at least one of an aromatic tricarboxylic acid represented by following Formula (7a) and an aromatic tricarboxylic acid monoanhydride represented by following Formula (7b):

[Chemical Formula 7]

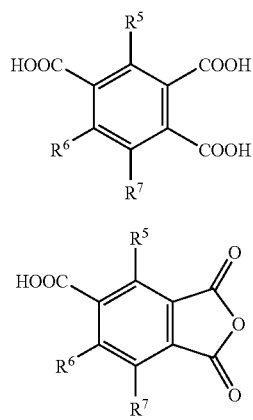

(7a)

(7b)

wherein $R^5$, $R^6$, and $R^7$ are the same as or different from one another and each represent hydrogen atom, a halogen atom, or an organic group, where two or more of $R^5$, $R^6$, and $R^7$ may be combined to form an aromatic or nonaromatic ring together with one or more carbon atoms constituting the benzene ring, in which the catalyst includes at least one cyclic imide compound derivable from at least one selected from the group consisting of a target product, a reaction intermediate, and a reaction byproduct and represented by following Formula (8):

[Chemical Formula 8]

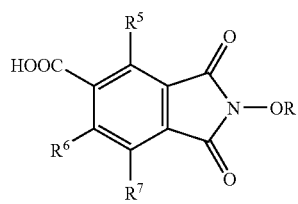

(8)

wherein $R^5$, $R^6$, and $R^7$ are the same as or different from one another and each represent hydrogen atom, a halogen atom, or an organic group, where two or more of $R^5$, $R^6$, and $R^7$ may be combined to form an aromatic or nonaromatic ring together with one or more carbon atoms constituting the benzene ring; and R represents hydrogen atom or an organic group, and the method includes the steps of producing the catalyst from at least one component selected from the group consisting of the target product, reaction intermediate, and reaction byproduct each formed as a result of the reaction, and using the produced catalyst in the oxidation reaction so as make up for a loss of the catalyst due to denaturation in the reaction. In this case, the catalyst is preferably produced from at least one component selected from the group consisting of an aromatic tricarboxylic acid represented by Formula (7a) and an aromatic tricarboxylic acid monoanhydride represented by Formula (7b) each formed as a result of the reaction and the produced catalyst is preferably used in the oxidation reaction.

The oxidation method of an organic compound according to the present invention can be a method for oxidizing a compound represented by following Formula (9):

[Chemical Formula 9]

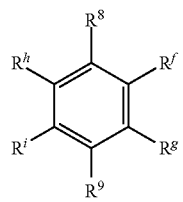
(9)

wherein $R^f$, $R^g$, $R^h$, and $R^i$ are the same as or different from one another and each represent a group convertible into carboxyl group upon oxidation; and $R^8$ and $R^9$ are the same as or different from each other and each represent hydrogen atom, a halogen atom, or an organic group, where two or more of $R^f$, $R^g$, $R^h$, $R^i$, $R^8$, and $R^9$ may be combined to form a nonaromatic ring together with one or more carbon atoms constituting the benzene ring, with oxygen to thereby yield at least one selected from the group consisting of an aromatic tetracarboxylic acid represented by following Formula (10a), an aromatic tetracarboxylic acid monoanhydride represented by following Formula (10b), and an aromatic tetracarboxylic acid dianhydride represented by following Formula (10c):

[Chemical Formula 10]

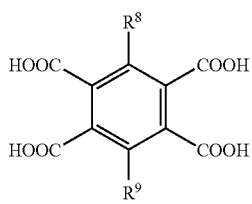
(10a)

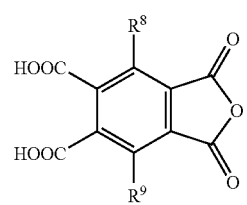
(10b)

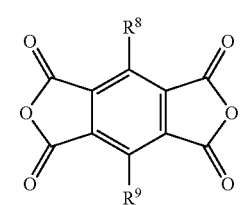
(10c)

wherein $R^8$ and $R^9$ are the same as or different from each other and each represent hydrogen atom, a halogen atom, or an organic group, in which the catalyst contains at least one of a cyclic imide compound represented by following Formula (11a) and a cyclic diimide compound represented by following Formula (11b), each being derivable from at least one selected from the group consisting of the target product, a reaction intermediate, and a reaction byproduct:

[Chemical Formula 11]

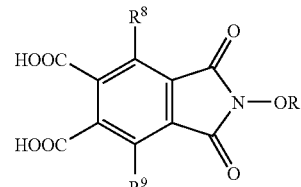
(11a)

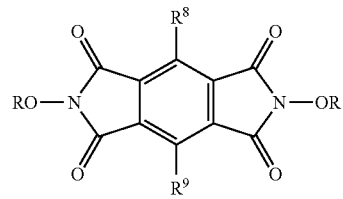
(11b)

wherein $R^8$ and $R^9$ are the same as or different from each other and each represent hydrogen atom, a halogen atom, or an organic group; and R represents hydrogen atom or an organic group, and the method includes the steps of producing the catalyst from at least one component selected from the group consisting of the target product, reaction intermediate, and reaction byproduct each formed as a result of the reaction, and using the produced catalyst in the oxidation reaction so as make up for a loss of the catalyst due to denaturation in the reaction. In this case, the catalyst is preferably produced from at least one component selected from the group consisting of the aromatic tetracarboxylic acid represented by Formula (10a), the aromatic tetracarboxylic acid monoanhydride represented by Formula (10b), and the aromatic tetracarboxylic acid dianhydride represented by Formula (10c), each formed as a result of the reaction, and the produced catalyst is preferably used in the oxidation reaction.

In addition, the present invention provides a process for producing an organic compound, which process includes the steps of (A) oxidizing an organic compound with oxygen by the catalysis of at least one N-hydroxy- or N-(substituted oxy)-imide compound derivable from at least one selected from the group consisting of a target product, a reaction intermediate, and a reaction byproduct, (B) separating the target product formed in Step A from at least one component selected from the group consisting of a target product, reaction intermediate, and reaction byproduct each formed as a result of the reaction and being to be used for producing the catalyst so as to make up for a loss of the catalyst due to denaturation in the reaction, (C) producing a catalyst using the at least one component separated in Step B, and (D) supplying the catalyst produced in Step C to Step A.

The production process can further include the step of (E) recovering an undenaturated catalyst from a reaction mixture and recycling the recovered undenaturated catalyst to Step A.

ADVANTAGES

According to the present invention, catalysts derivable from at least one selected from the group consisting of a target product, a reaction intermediate, and a reaction byproduct catalyst are used, and the catalysts are produced from at least one component selected from the target product, reaction intermediate and reaction byproduct each formed as a result of the reaction, and the produced catalysts are used in the oxidation reaction so as to make up for losses of the catalysts denaturated in the course of reaction. Such target products must be separated from the reaction mixture somehow so as to yield products. Likewise, reaction intermediates must be separated so as to return to the reaction system, and reaction byproducts must be separated so as to be wasted. This separation step is an essentially necessary step regardless of whether or not they are supplied to the production of catalyst imide compounds. The amounts of these components are generally larger than those of catalysts. Accordingly, losses of the catalysts due to denaturation can be very easily made up for, since the catalysts can be produced using only part of the target product, reaction intermediate, and/or reaction byproduct each formed as a result of the reaction. In addition, there is no need of isolating denaturated catalysts alone which exist in trace amounts. Accordingly, the present invention can easily, conveniently, and inexpensively make up for a loss of a catalyst N-hydroxy- or N-(substituted oxy)-imide compound denaturated in the course of oxidation of organic compounds with oxygen in the presence of the catalyst.

EXPLANATIONS OF LETTERS OR NUMERALS

Figure 1:
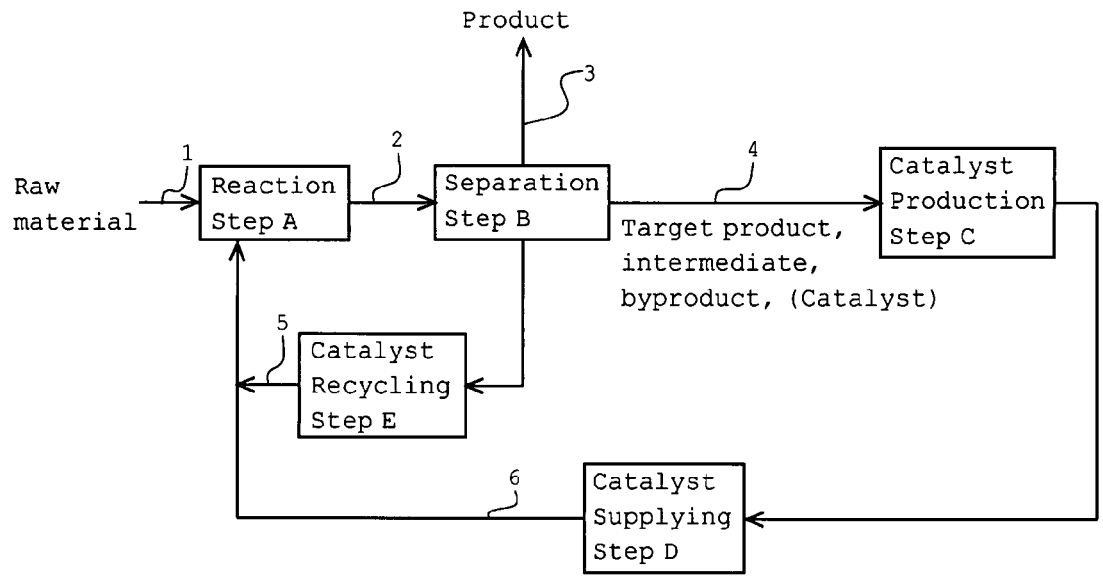
FIG. 1 is a schematic process chart as an embodiment of the production process of organic compounds according to the present invention.
Figure 2:
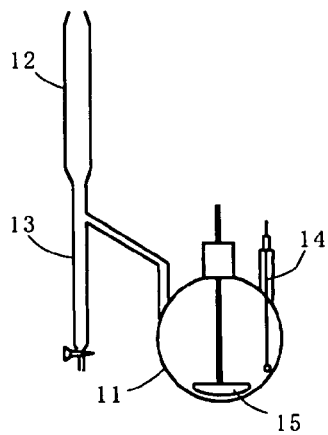
FIG. 2 is a schematic diagram of a catalyst production system used in Examples.

11 Flask
12 Reflux Condenser
13 Dean-Stark Fractionating Unit
14 Thermometer
15 Agitating Blade

BEST MODE FOR CARRYING OUT THE INVENTION

Organic compounds for use in the present invention as raw materials are not specifically limited, as long as they are such organic compounds that at least one N-hydroxy- or N-(substituted oxy)-imide compound such as a cyclic N-hydroxy- or N-(substituted oxy)-imide compound can be induced from at least one of target products, reaction intermediates (reaction intermediates derived from raw materials), and reaction byproducts (reaction byproducts derived from raw materials), each formed upon oxidation with oxygen. According to the present invention, N-hydroxy- or N-(substituted oxy)-imide compounds such as cyclic N-hydroxy- or N-(substituted oxy)-imide compounds are used as catalysts.

Representative examples of organic compounds used as the raw materials include the compounds represented by Formula (1), the compounds represented by Formula (3), the compounds represented by Formula (6), and the compounds represented by Formula (9).

In the compounds represented by Formula (1), "n" represents an integer of 4 to 20. The ring shown of Formula (1) may have one or more substituents. The repetition number "n" is preferably an integer of 5 to 15 and more preferably 5, 6, 12 or 15. Examples of the substituents which the ring (cycloalkane ring) of Formula (1) may have include halogen atoms, alkyl groups which may have one or more halogen atoms, cycloalkyl groups, aryl groups, alkoxy groups which may have one or more halogen atoms, protected or unprotected hydroxyl group, protected or unprotected hydroxy(halo)alkyl groups, protected or unprotected amino groups, protected or unprotected carboxyl group, protected or unprotected sulfo group, protected or unprotected acyl groups, cyano group, nitro group, and oxo group ($=O$). Protecting groups conventionally used in organic synthesis can be used herein.

The halogen atoms include fluorine atom, chlorine atom, bromine atom, and iodine atom. Examples of the alkyl groups which may have one or more halogen atoms include alkyl groups each having about one to about fifteen carbon atoms, such as methyl, ethyl, propyl, isopropyl, butyl, isobutyl, t-butyl, and hexyl groups, of which alkyl groups having about one to about ten carbon atoms are preferred, and alkyl groups having about one to about six carbon atoms are more preferred; and haloalkyl groups having about one to about fifteen carbon atoms, such as trifluoromethyl and pentafluoroethyl groups, of which haloalkyl groups having about one to about ten carbon atoms are preferred, and haloalkyl groups having about one to about six carbon atoms are more preferred. The cycloalkyl groups include, for example, cycloalkyl groups having about three to about fifteen members, such as cyclopentyl group and cyclohexyl group. Examples of the aryl groups are phenyl and naphthyl groups. The alkoxy groups which may have one or more halogen atoms include, for example, alkoxy groups having about one to about fifteen carbon atoms, such as methoxy, ethoxy, propoxy, isopropoxy, butoxy, t-butyloxy, and hexyloxy groups, of which alkoxy groups having about one to about ten carbon atoms are preferred, and alkoxy groups having about one to about six carbon atoms are more preferred; and haloalkoxy groups having about one to about fifteen carbon atoms, such as trifluoromethoxy group, of which haloalkoxy groups having about one to about ten carbon atoms are preferred, and haloalkoxy groups having about one to about six carbon atoms are more preferred. Examples of the hydroxy(halo)alkyl groups include hydroxymethyl, hydroxyethyl, hydroxypropyl, 1-hydroxy-1-methylethyl, and 2,2,2-trifluoro-1-trifluoromethyl-1-hydroxyethyl groups, of which hydroxyalkyl groups having about one to about four carbon atoms and hydroxy-(haloalkyl) groups having about one to about four carbon atoms are preferred. The acyl groups include aliphatic acyl groups having about one to about six carbon atoms, such as formyl, acetyl, propionyl, butyryl, isobutyryl, and pivaloyl groups; acetoacetyl group; and aromatic acyl groups such as benzoyl group.

Of the compounds represented by Formula (1), compounds having no substituent on the cycloalkane ring (cycloalkanes), and compounds having one or more alkyl groups having one to six carbon atoms, such as methyl group, on the cycloalkane ring are preferred. Representative examples of the compounds represented by Formula (1) are cyclohexane, cyclopentane, cyclododecane, and cyclopentadecane.

Oxidation of compounds represented by Formula (1) with oxygen by the catalysis of a N-hydroxy- or N-(substituted oxy)-imide compound yields corresponding cycloalkanones, cycloalkanols, and/or dicarboxylic acids having carbon atoms in the number of "n" in principal chain as main products. The proportions of these products can be controlled by appropriately setting the reaction conditions such as type and amount of the catalyst, reaction temperature, and reaction time. The reaction also yields, as byproducts, dicarboxylic acids having carbon atoms in a number of less than "n" in principal chain.

When cyclohexane, for example, is used as the compound represented by Formula (1), cyclohexanone, cyclohexanol, or adipic acid, or a mixture of them is mainly produced, and succinic acid and/or glutaric acid, for example, is by-produced. When cyclopentane is used as the compound represented by Formula (1), cyclopentanone, cyclopentanol or glutaric acid, or a mixture of them is mainly produced, and succinic acid, for example, is by-produced. When cyclododecane is used as the compound represented by Formula (1), cyclododecanone, cyclododecanol, or dodecanedioic acid, or a mixture of them is mainly produced, and succinic acid and/or glutaric acid, for example, is by-produced.

To produce a corresponding cycloalkanone, a corresponding cycloalkanol or a corresponding dicarboxylic acid having carbon atoms in the number of "n" in principal chain, or a mixture of them using the compound of Formula (1) as a raw material, the cyclic N-hydroxy- or N-(substituted oxy)-imide compound represented by Formula (2) and derivable from at least one selected from the group consisting of a target product, a reaction intermediate, and a reaction byproduct is used as the catalyst, and the catalyst is produced from at least one component selected from the group consisting of the target product, reaction intermediate, and reaction byproduct each formed as a result of the reaction and the produced catalyst is used in the oxidation reaction so as make up for a loss of the catalyst due to denaturation in the reaction.

In Formula (2), "m" is an integer of 2 or more and (n−2) or less. The repetition number "m" is preferably 2 or 3. R represents hydrogen atom or an organic group. The organic group in R is preferably a group that can be converted into hydrogen atom under reaction conditions upon, for example, hydrolysis. Examples of such organic groups include alkyl groups including alkyl groups having about one to about four carbon atoms, such as methyl and t-butyl groups, alkenyl groups such as allyl group, cycloalkyl groups such as cyclohexyl group, aryl groups such as 2,4-dinitrophenyl group, aralkyl groups such as benzyl, 2,6-dichlorobenzyl, and triphenylmethyl groups; groups that can form acetal or hemiacetal group with an adjacent oxygen atom, including substituted methyl groups such as methoxymethyl, methylthiomethyl, benzyloxymethyl, t-butoxy methyl, and 2-methoxyethoxymethyl groups, substituted ethyl groups such as 1-ethoxyethyl, 1-methyl-1-methoxyethyl, and 2-methoxyethyl groups; tetrahydropyranyl group, tetrahydrofuranyl group, 1-hydroxyalkyl groups such as 1-hydroxyethyl and 1-hydroxyhexyl groups; acyl groups (e.g., aliphatic saturated or unsaturated acyl groups inclusive of aliphatic acyl groups having about one to about twenty carbon atoms, such as formyl, acetyl, propionyl, butyryl, isobutyryl, valeryl, pivaloyl, hexanoyl, heptanoyl, octanoyl, nonanoyl, decanoyl, lauroyl, myristoyl, palmitoyl, and stearoyl groups, of which aliphatic acyl groups having about one to about six carbon atoms are preferred; acetoacetyl group; alicyclic acyl groups including cycloalkanecarbonyl groups such as cyclopentanecarbonyl and cyclohexanecarbonyl groups; aromatic acyl groups such as benzoyl and naphthoyl groups); sulfonyl groups such as methanesulfonyl, ethanesulfonyl, trifluoromethanesulfonyl, benzenesulfonyl, p-toluenesulfonyl, and naphthalenesulfonyl groups, alkoxycarbonyl groups including ($C_1$-$C_4$ alkoxy)-carbonyl groups such as methoxycarbonyl, ethoxycarbonyl, and t-butoxycarbonyl groups, aralkyloxycarbonyl groups such as benzyloxycarbonyl group and p-methoxybenzyloxycarbonyl group, substituted or unsubstituted carbamoyl groups such as carbamoyl, methylcarbamoyl, and phenylcarbamoyl groups, groups corresponding to an inorganic acid (e.g., sulfuric acid, nitric acid, phosphoric acid, or boric acid), except that hydroxyl group (OH group) is removed therefrom, and substituted silyl groups such as trimethylsilyl, t-butyldimethylsilyl, tribenzylsilyl, and triphenylsilyl groups.

Preferred examples of R include hydrogen atom; groups that can form acetal or hemiacetal group with an adjacent oxygen atom; groups that can be easily converted into hydrogen atom upon hydrolysis, including groups corresponding to an acid such as carboxylic acid, sulfonic acid, carbonic acid, carbamic acid, sulfuric acid, phosphoric acid, or boric acid, except that OH group is removed therefrom, such as acyl groups, sulfonyl groups, alkoxycarbonyl groups, and carbamoyl groups. Among them, R is especially preferably represents hydrogen atom or an acyl group. Of such acyl groups, aliphatic acyl groups having about one to about twenty carbon atoms are preferred, and aliphatic acyl groups having about one to about six carbon atoms are more preferred.

The ring shown of Formula (2) may have one or more substituents. The substituents herein are as the substituents which the ring shown of Formula (1) may have.

Representative examples of the cyclic imide compounds represented by Formula (2) are compounds derivable from succinic acid, including N-hydroxysuccinimide and N-(substituted oxy) succinimides such as N-acetoxysuccinimide; and compounds derivable from glutaric acid, including N-hydroxyglutarimide and N-(substituted oxy) glutarimides such as N-acetoxyglutarimide. These compounds can be advantageously used as a catalyst when, of the compounds represented by Formula (1), cycloalkanes such as cyclohexane, cyclopentane, and cyclododecane are used as a raw material.

When a compound represented by Formula (1) is used as a raw material in the oxidation reaction, the target product, reaction intermediate, and/or reaction byproduct each formed as a result of the reaction and is used for the production of catalyst can be any of dicarboxylic acids having carbon atoms in the number of "n" in principal chain corresponding to the compound of Formula (1) used as the raw material (main products); and dicarboxylic acids having carbon atoms in a number less than "n" (byproducts). Particularly, succinic acid and/or glutaric acid is preferred as the raw material for the catalyst, when, of the compounds represented by Formula (1), cycloalkanes such as cyclohexane, cyclopentane, and cyclododecane are used as the raw material.

In the compounds represented by Formula (3), $R^a$ and $R^b$ are the same as or different from one another and each represent a group convertible into carboxyl group upon oxidation. Examples of the group convertible into carboxyl group upon oxidation include organic groups having a carbon-hydrogen bond at the benzyl position of the aromatic ring, such as alkyl groups, lower-order oxidized groups derived from alkyl groups (lower-order oxidized groups corresponding to alkyl groups, except with a carbon atom at the 1-position of alkyl groups being not oxidized to carboxyl group or an equivalent thereof), and cycloalkyl groups.

The alkyl groups include primary or secondary alkyl groups such as methyl, ethyl, propyl, isopropyl, butyl, isobutyl, s-butyl, pentyl, isopentyl, hexyl, isohexyl, heptyl, octyl, 2-ethylhexyl, and decyl groups. Among them, alkyl groups having about one to about four carbon atoms are preferred, of which alkyl groups having about one to about three carbon atoms, such as methyl group, ethyl group, and isopropyl group, are especially preferred. The lower-order oxidized groups derived from alkyl groups include hydroxyalkyl groups, formyl group, formylalkyl groups, and alkyl groups having oxo group. Examples of the hydroxyalkyl groups include hydroxy-alkyl groups having about one to about six carbon atoms, such as hydroxymethyl, 1-hydroxyethyl, 1-hydroxypropyl, 1-hydroxy-1-methylethyl, and 1-hydroxybutyl groups. Examples of the formylalkyl groups include formyl-($C_1$-$C_6$ alkyl) groups such as formylmethyl, 1-formylethyl, and 1-formylpropyl groups. Examples of the alkyl groups having oxo group include aliphatic acyl groups including aliphatic acyl groups having about one to about six carbon atoms, such as acetyl, propionyl, butyryl, pentanoyl, and hexanoyl groups. Among them, lower-order oxidized groups corresponding to alkyl groups having about one to about four carbon atoms are preferred, and those corresponding to alkyl groups having about one to about three carbon atoms are more preferred. Examples of the cycloalkyl groups are cyclopentyl group and cyclohexyl group. These alkyl groups, lower-order oxidized groups thereof, and cycloalkyl groups may each have one or more substituents within ranges not adversely affecting the reaction. As the substituents $R^a$ and $R^b$, methyl group is typically preferred.

In Formula (3), $R^1$, $R^2$, $R^3$, and $R^4$ are the same as or different from one another and each represent hydrogen atom, a halogen atom, or an organic group. Examples of the halogen atom are fluorine atom, chlorine atom, and bromine atom. The organic group can be any group that does not adversely affect the oxidation reaction and includes, for example, halogen atoms, alkyl groups which may have one or more halogen atoms, phenyl group, protected or unprotected hydroxyl group, and alkoxy groups which may have one or more halogen atoms. The halogen atoms, alkyl groups which may have one or more halogen atom, protected or unprotected hydroxyl group, and alkoxy groups which may have one or more halogen atoms can be the same as the substituents which the ring shown of Formula (1) may have.

In Formula (3), two or more of $R^a$, $R^b$, $R^1$, $R^2$, $R^3$, and $R^4$ may be combined to form an aromatic or nonaromatic ring together with one or more carbon atoms constituting the benzene ring. Examples of the aromatic ring are benzene ring and naphthalene ring. Examples of the nonaromatic ring include cycloalkene rings, of which 5 or 6-membered cycloalkene rings are preferred; rings constituting cyclic ethers, of which those constituting 5 or 6-membered cyclic ethers, such as dihydrofuran ring and dihydropyran ring, are preferred; and lactone rings, of which 5 or 6-membered lactone rings are preferred.

Representative examples of the compounds represented by Formula (3) are ortho-xylene, ortho-xylylene glycol, ortho-phthalaldehyde, indan, and tetralin.

When a compound represented by Formula (3) is oxidized with oxygen by the catalysis of a N-hydroxy- or N-(substituted oxy)-imide compound, the corresponding aromatic dicarboxylic acid represented by Formula (4a), aromatic dicarboxylic acid anhydride represented by Formula (4b), or a mixture of them is obtained. The proportions of these products can be controlled by appropriately setting the reaction conditions such as type and amount of the catalyst, reaction temperature, reaction time, and the presence or absence of dehydration operation.

In Formulae (4a) and (4b), $R^1$, $R^2$, $R^3$, and $R^4$ are the same as or different from one another and each represent hydrogen atom, a halogen atom, or an organic group. Two or more of $R^1$, $R^2$, $R^3$, and $R^4$ may be combined to form an aromatic or nonaromatic ring together with one or more carbon atoms constituting the benzene ring. The halogen atom, organic group, and aromatic or nonaromatic ring are as in Formula (3). When ortho-xylene, ortho-xylylene glycol, ortho-phthalaldehyde, indan, or tetralin, for example, is used as the compound represented by Formula (3), ortho-phthalic acid, ortho-phthalic acid anhydride (anhydrous ortho-phthalic acid), or a mixture of them is obtained as a main product.

To produce a corresponding aromatic dicarboxylic acid, aromatic dicarboxylic acid anhydride, or a mixture of them using the compound of Formula (3) as a raw material, the cyclic N-hydroxy- or N-(substituted oxy)-imide compound represented by Formula (5) and derivable from at least one selected from the group consisting of the target product, a reaction intermediate, and a reaction byproduct is used as the catalyst, the catalyst is produced from at least one component selected from the group consisting of the target product, reaction intermediate, and reaction byproduct each formed as a result of the reaction and the produced catalyst is used in the oxidation reaction so as make up for a loss of the catalyst due to denaturation in the reaction.

In Formula (5), $R^1$, $R^2$, $R^3$, and $R^4$ are the same as or different from one another and each represent hydrogen atom, a halogen atom, or an organic group. Two or more of $R^1$, $R^2$, $R^3$, and $R^4$ may be combined to form an aromatic or nonaromatic ring together with one or more carbon atoms constituting the benzene ring. These halogen atom, organic group, and aromatic or nonaromatic ring are as in Formula (3). The substituent R of Formula (5) represents hydrogen atom or an organic group. The organic group is as the organic groups in R of Formula (2).

Representative examples of the cyclic imide compounds represented by Formula (5) are compounds derivable from ortho-phthalic acid or ortho-phthalic anhydride, including N-hydroxyphthalimide; and N-(substituted oxy)phthalimides such as N-acetoxyphthalimide. These compounds can be advantageously used as the catalyst when, of the compounds represented by Formula (3), ortho-xylene, ortho-xylylene glycol, ortho-phthalaldehyde, indan, or tetralin is used as a raw material.

When a compound represented by Formula (3) is used as a raw material in the oxidation reaction, the target product, reaction intermediate, and/or reaction byproduct each formed as a result of the reaction and to be used in production of the catalyst includes a compound represented by Formula (4a), a compound represented by Formula (4b), and a mixture of them, each corresponding to the compound of Formula (3) used as the raw material in the oxidation reaction. Among them, ortho-phthalic acid and/or ortho-phthalic anhydride is preferred for the production of the catalyst when, of the compounds of Formula (3), ortho-xylene, ortho-xylylene glycol, ortho-phthalaldehyde, indan, or tetralin is used as the raw material.

$R^k$ of Formula (3), $R^k$ in Formulae (4a) and (4b), and $R^k$ of Formula (5), wherein k is 1, 2, 3 or 4, may be the same as or different from one another, as they may change in the course of the oxidation reaction or the production of catalyst.

In the compounds represented by Formula (6), $R^c$, $R^d$, and $R^e$ are the same as or different from one another and each represent a group convertible into carboxyl group upon oxidation; and $R^5$, $R^6$, and $R^7$ are the same as or different from one another and each represent hydrogen atom, a halogen atom, or an organic group. Two or more of $R^c$, $R^d$, $R^e$, $R^5$, $R^6$, and $R^7$ may be combined to form an aromatic or nonaromatic ring together with one or more carbon atoms constituting the benzene ring. The group convertible into carboxyl group upon oxidation is as in the groups convertible into carboxyl group upon oxidation in $R^a$ and $R^b$ of Formula (3). The halogen atom and organic group are as the halogen atoms and organic groups in $R^1$, $R^2$, $R^3$, and $R^4$ of Formula (3). The aromatic or nonaromatic ring is as the rings formed by two or more of $R^a$, $R^b$, $R^1$, $R^2$, $R^3$, and $R^4$ with one or more carbon atoms constituting the benzene ring of Formula (3).

Representative examples of the compounds of Formula (6) are 1,2,4-trimethylbenzene, 1,2,4-tris(hydroxymethyl)benzene, and 1,2,4-triformylbenzene.

When a compound represented by Formula (6) is oxidized with oxygen by the catalysis of a N-hydroxy- or N-(substituted oxy)-imide compound, the corresponding aromatic tricarboxylic acid represented by Formula (7a), aromatic tricarboxylic acid monoanhydride represented by Formula (7b), or a mixture of them is produced. The proportions of these products can be controlled by appropriately setting the reaction conditions such as type and amount of the catalyst, reaction temperature, reaction time, and the presence or absence of dehydration operation.

In Formulae (7a) and (7b), $R^5$, $R^6$, and $R^7$ are the same as or different from one another and each represent hydrogen atom, a halogen atom, or an organic group. Two or more of $R^5$, $R^6$, and $R^7$ may be combined to form an aromatic or nonaromatic ring together with one or more carbon atoms constituting the benzene ring. The halogen atom, organic group, and aromatic or nonaromatic ring herein are as in Formula (6). When 1,2,4-trimethylbenzene, 1,2,4-tris(hydroxymethyl)benzene, and/or 1,2,4-triformylbenzene, for example, is used as the compound represented by Formula (6), trimellitic acid, trimellitic anhydride, or a mixture of them is obtained as a main product.

To produce a corresponding aromatic tricarboxylic acid, aromatic tricarboxylic acid anhydride, or a mixture of them using the compound of Formula (6) as a raw material, a cyclic N-hydroxy- or N-(substituted oxy)-imide compound represented by Formula (8) and derivable from at least one selected from the group consisting of the target product, a reaction intermediate, and a reaction byproduct is used as the catalyst, the catalyst is produced from at least one component selected from the group consisting of the target product, reaction intermediate, and reaction byproduct each formed as a result of the reaction, and the produced catalyst is used in the oxidation reaction so as make up for a loss of the catalyst due to denaturation in the reaction.

In Formula (8), $R^5$, $R^6$, and $R^7$ are the same as or different from one another and each represent hydrogen atom, a halogen atom, or an organic group. Two or more of $R^5$, $R^6$, and $R^7$ may be combined to form an aromatic or nonaromatic ring together with one or more carbon atoms constituting the benzene ring. These halogen atom, organic group, and aromatic or nonaromatic ring are as in Formula (6). R of Formula (8) represents hydrogen atom or an organic group. The organic group herein is as the organic groups in R of Formula (2).

Representative examples of the cyclic imide compounds of Formula (8) are compounds derivable from trimellitic acid or trimellitic anhydride, including 2-carboxy-N-hydroxyphthalimide; and 2-carboxy-N-(substituted oxy)phthalimides such as 2-carboxy-N-acetoxyphthalimide. These compounds can be advantageously used as the catalyst when, of the compounds represented by Formula (6), 1,2,4-trimethylbenzene, 1,2,4-tris(hydroxymethyl)benzene, and/or 1,2,4-triformylbenzene is used as the raw material.

When a compound represented by Formula (6) is used as the raw material in the oxidation reaction, the target product, reaction intermediate, and/or reaction byproduct each formed as a result of the reaction to be used in the production of catalyst includes a compound represented by Formula (7a), a compound represented by Formula (7b), and a mixture of them, each corresponding to the compound of Formula (6) used as the raw material. Specifically, trimellitic acid and/or trimellitic anhydride is preferred for the production of the catalyst when, of the compounds represented by Formula (6), 1,2,4-trimethylbenzene, 1,2,4-tris(hydroxymethyl)benzene, and/or 1,2,4-triformylbenzene is used as the raw material in the oxidation reaction.

$R^p$ of Formula (6), $R^p$ in Formulae (7a) and (7b), and $R^p$ of Formula (8), wherein p is 5, 6 or 7, may be the same as or different from one another, since they may change in the course of the oxidation reaction or the production of catalyst.

In the compounds represented by Formula (9), $R^f$, $R^g$, $R^h$, and $R^i$ are the same as or different from one another and each represent a group convertible into carboxyl group upon oxidation. $R^8$ and $R^9$ are the same as or different from each other and each represent hydrogen atom, a halogen atom, or an organic group. Two or more of $R^f$, $R^g$, $R^h$, $R^i$, $R^8$, and $R^9$ may be combined to form a nonaromatic ring together with one or more carbon atoms constituting the benzene ring. The group convertible into carboxyl group upon oxidation is as the groups convertible into carboxyl group upon oxidation in $R^a$ and $R^b$ of Formula (3). The halogen atom and organic group are as the halogen atoms and organic groups in $R^1$, $R^2$, $R^3$, and $R^4$ of Formula (3). The aromatic or nonaromatic ring herein is as the rings formed by two or more of $R^a$, $R^b$, $R^1$, $R^2$, $R^3$, and $R^4$ with one or more carbon atoms constituting the benzene ring, of Formula (3).

Representative examples of the compounds of Formula (9) are 1,2,4,5-tetramethylbenzene (durene), 1,2,4,5-tetrakis(hydroxymethyl)benzene, and 1,2,4,5-tetraformylbenzene.

When a compound represented by Formula (9) is oxidized with oxygen by the catalysis of a cyclic N-hydroxy- or N-(substituted oxy)-imide compound, a corresponding aromatic tetracarboxylic acid represented by Formula (10a), aromatic tetracarboxylic acid monoanhydride represented by Formula (10b), aromatic tetracarboxylic acid dianhydride represented by Formula (10c), or a mixture of them is obtained. The proportions of these products can be controlled by appropriately setting the reaction conditions such as type and amount of the catalyst, reaction temperature, reaction time, and the presence or absence of dehydration operation.

In Formulae (10a), (10b), and (10c), $R^8$ and $R^9$ are the same as or different from each other and each represent hydrogen atom, a halogen atom, or an organic group. The halogen atom and organic group are as in Formula (9). When 1,2,4,5-tetramethylbenzene (durene), 1,2,4,5-tetrakis(hydroxymethyl)benzene, and/or 1,2,4,5-tetraformylbenzene, for example, is used as the compound represented by Formula (9), pyromellitic acid, monoanhydrous pyromellitic acid (pyromellitic monoanhydride), dianhydrous pyromellitic acid (pyromellitic dianhydride), or a mixture of them can be obtained as a main product.

To produce a corresponding aromatic tetracarboxylic acid, aromatic tetracarboxylic acid monoanhydride, aromatic tetracarboxylic acid dianhydride, or a mixture of them using a compound of Formula (9) as a raw material, the cyclic imide compound represented by Formula (11a) and/or the cyclic diimide compound represented by Formula (11b), each derivable from at least one selected from the group consisting of the target product, a reaction intermediate, and a reaction byproduct, is used as the catalyst, the catalyst is produced from at least one component selected from the group consisting of the target product, reaction intermediate, and reaction byproduct each formed as a result of the reaction, and the produced catalyst is used in the oxidation reaction, so as make up for a loss of the catalyst due to denaturation in the reaction.

In Formulae (11a) and (11b), $R^8$ and $R^9$ are the same as or different from each other and each represent hydrogen atom, a halogen atom, or an organic group. These halogen atoms and organic groups are as in Formula (9). The substituent R in Formula (11a) represents hydrogen atom or an organic group. The organic groups herein are as the organic groups in R of Formula (2).

Representative examples of the cyclic imide compounds of Formula (11a) are compounds derivable from pyromellitic acid and/or pyromellitic monoanhydride, such as N-hydroxypyromellitimide; and N-(substituted oxy)pyromellitimides such as N-acetoxypyromellitimide. Representative examples of the cyclic diimide compounds of Formula (11b) are compounds derivable from pyromellitic acid, pyromellitic monoanhydride, and/or pyromellitic dianhydride, such as N,N'-dihydroxypyromellitic diimide; and N,N'-diacetoxypyromellitic diimide. These compounds can be advantageously used as the catalyst when, of the compounds of Formula (9), 1,2,4,5-tetramethylbenzene (durene), 1,2,4,5-tetrakis(hydroxymethyl)benzene, and/or 1,2,4,5-tetraformylbenzene is used as the raw material in the oxidation reaction.

When a compound represented by Formula (9) is used as the raw material in the oxidation reaction, the target product, reaction intermediate, and reaction byproduct, each formed as a result of the reaction, for use in the production of catalyst include a compound represented by Formula (10a), a compound represented by Formula (10b), and a mixture of them, each corresponding to the compound of Formula (9) used as the raw material. Among them, at least one selected from the group consisting of pyromellitic acid, pyromellitic monoanhydride, and pyromellitic dianhydride is preferred for the production of the catalyst when, of the compounds represented by Formula (9), 1,2,4,5-tetramethylbenzene (durene), 1,2,4,5-tetrakis(hydroxymethyl)benzene, and/or 1,2,4,5-tetraformylbenzene, for example, is used as the raw material in the oxidation reaction.

$R^q$ of Formula (9), $R^q$ in Formulae (10a), (10b), and (10c), and $R^q$ in Formulae (11a) and (11b), wherein q is 8 or 9, may be the same as or different from one another, since they may change in the course of the oxidation reaction or the production of catalyst.

The oxygen for use in the oxidation reaction in the present invention can be molecular oxygen. The molecular oxygen can be any of pure oxygen, diluted oxygen with an inert gas such as nitrogen, argon, or helium gas, and the air.

One or more promoters (co-catalysts) can be used in combination with the catalyst N-hydroxy- or N-(substituted oxy)-imide compound in the oxidation reaction. The promoters (co-catalysts) can be any of compounds comprising transition metals or Group 13 elements of the Periodic Table of Elements. Examples of such compounds are oxides, hydroxides, nitrides, oxoacids or salts thereof, oxoacid esters, heteropolyacids or salts thereof, organic acid salts, inorganic acid salts, halides, and complexes. Each of these promoters can be used alone or in combination. Examples of the transition metal elements are, of the Periodic Table of Elements, Group 3 elements including scandium (Sc), yttrium (Y), as well as lanthanoid elements such as cerium (Ce) and samarium (Sm), and actinoid elements such as actinium (Ac); Group 4 elements such as titanium (Ti) and zirconium (Zr); Group 5 elements such as vanadium (V) and niobium (Nb); Group 6 elements such as chromium (Cr), molybdenum (Mo), and tungsten (W); Group 7 elements such as manganese (Mn), technetium (Tc), and rhenium (Re); Group 8 elements such as iron (Fe) and ruthenium (Ru); Group 9 elements such as cobalt (Co) and rhodium (Rh); Group 10 elements such as nickel (Ni), palladium (Pd), and platinum (Pt); and Group 11 elements such as copper (Cu). Preferred elements include Ce, V, Nb, Cr, Mo, W, Mn, Fe, Ru, Co, Rh, Ni, and Cu. The Group 13 elements include boron (B), and aluminum (Al). Especially preferred promoters (co-catalysts) include divalent or trivalent cobalt compounds such as cobalt acetate and cobalt acetylacetonate; divalent or trivalent manganese compounds such as manganese acetate and manganese acetylacetonate; and zirconium compounds such as zirconium oxoacetate.

The amount of the catalyst N-hydroxy- or N-(substituted oxy)-imide compound can be selected within a broad range and is, for example, about 0.0000001 to about 1 mole, preferably about 0.000001 to about 0.5 mole, more preferably about 0.00001 to about 0.4 mole, and frequently about 0.0001 to about 0.35 mole, per 1 mole of the raw material organic compound (substrate). The amount of the promoter (co-catalyst) is, for example, about 0.001 to about 20 moles, and preferably about 0.005 to about 10 moles, per 1 mole of the catalyst N-hydroxy- or N-(substituted oxy)-imide compound. The amount of the promoter (co-catalyst) is, for example, about 0.00001 percent by mole to about 10 percent by mole, and preferably about 0.1 percent by mole to about 5 percent by mole, relative to the substrate. The catalyst and the promoter may be supplied to the reaction system in one process, continuously, or intermittently.

The reaction temperature in the oxidation reaction can be set according typically to the types of the raw materials, catalyst and promoter, if used, and is, for example, about 0° C. to about 300° C., preferably about 30° C. to about 250° C., and more preferably about 40° C. to about 200° C. The oxidation reaction is generally often carried out at about 40° C. to about 150° C. The oxidation reaction can be carried out under atmospheric pressure (normal pressure) or under a pressure (under a load).

When the target product is an acid anhydride such as a cyclic acid anhydride, the reaction can be conducted while adding a dehydrating agent to the oxidation reaction system and/or distilling off by-produced water so as to accelerate the reaction. Examples of the dehydrating agent are acid anhydrides such as acetic anhydride. Alternatively, the oxidation reaction and dehydration reaction can be carried out stepwise. For example, the target acid anhydride can be formed by forming a carboxylic acid, such as a polycarboxylic acid, upon oxidation reaction, and then conducting a dehydration reaction while adding a dehydrating agent to the reaction system or distilling off by-produced water. When the target product is a polyanhydride having two or more acid anhydride groups, such as a dianhydride, the target polyanhydride may be formed by forming a monoanhydride as a result of an oxidation reaction and dehydration reaction, and then repeating the procedure of an oxidation reaction and a dehydration reaction. The "at least one component selected from the group consisting of the target product, reaction intermediate, and reaction byproduct each formed as a result of the reaction" for use as a raw material for the production of catalyst in the present invention also includes such target products, reaction intermediates, and reaction by-products obtained as a result of an oxidation reaction and a subsequent dehydration reaction carried out stepwise as above.

The method for producing the catalyst N-hydroxy- or N-(substituted oxy)-imide compound from at least one component selected from the group consisting of the target product, reaction intermediate, and reaction byproduct each formed as a result of the reaction is not specifically limited and can be conducted according to a known synthesis process of imide compounds or using a known reaction.

The target products, reaction intermediates, and reaction byproducts for use in the production of catalyst can be highly pure substances that have been highly purified from a reaction mixture but can also be a reaction mixture taken out from an oxidation reactor without purification, or a mixture with another component which can be obtained from the reaction mixture after carrying out a simple separation and purification operation (or device). The catalyst N-hydroxy- or N-(substituted oxy)-imide compound may be produced from at least one component selected from the group consisting of the target compound reaction intermediate, and reaction byproduct each formed as a result of the reaction outside the oxidation reaction system as above. Alternatively or in addition, the catalyst may be produced from the at least one component in the oxidation reaction system (in situ).

When the catalyst is produced using a target product, a highly pure catalyst imide compound can be obtained by using part of the target product, since the target product has been highly purified so as to yield a final product. In contrast, a reaction intermediate or a reaction byproduct is often extracted as a mixture with one or more other components from the reaction mixture (crude reaction mixture). Thus, it is economically preferred to use these components for the production of catalyst not after further purifying the mixture but as the mixture with one or more other components without purification. For example, when the catalyst imide compound is induced from a reaction intermediate, the reaction intermediate is often recycled to the reaction system together with an unreacted raw material, catalyst, solvent, and other reaction intermediates after recovering all or part of the target product and all or part of byproducts from the crude reaction mixture. The mixture of the reaction intermediate, unreacted raw material, catalyst, solvent, and other reaction intermediates (or a mixture of some of these components) is preferably used for the production of catalyst. When the other components than the reaction intermediate in the mixture include a component that inhibits the catalyst synthesis reaction, the mixture may be subjected to a suitable treatment before the production of catalyst. Likewise, a reaction byproduct is often recovered with other reaction byproducts from the crude reaction mixture. Accordingly, when the catalyst imide compound is derived from the reaction byproduct, the mixture is preferably used for the production of catalyst. When the other components than the reaction byproduct in the mixture include a component that inhibits the catalyst synthesis reaction, the mixture may be subjected to a suitable treatment before the production of catalyst. The target product with one or more reaction intermediates, or the target product with one or more reaction byproducts can be used for the production of catalyst.

The target product, reaction intermediate, and reaction byproduct for the production of catalyst are not specifically limited, as long as they can be used in the production of catalyst. Preferred examples of these components for easy reaction are carboxylic acids including monocarboxylic acids such as acetic acid and benzoic acid; dicarboxylic acids such as succinic acid, glutaric acid, ortho-phthalic acid, and terephthalic acid; tricarboxylic acids such as trimellitic acid; tetracarboxylic acids such as pyromellitic acid; corresponding acid anhydrides to these carboxylic acids, of which cyclic acid anhydrides are preferred; and mixtures of them. Among them, polycarboxylic acids, corresponding polycarboxylic acid anhydrides, and mixtures of them are preferred, and polycarboxylic acids that can form cyclic acid anhydrides, corresponding cyclic acid anhydrides, and mixtures of them are more preferred.

For example, a N-hydroxyimide compound can be easily produced by reacting a hydroxylamine with a carboxylic acid (for example, a polycarboxylic acid) or a carboxylic acid anhydride (for example, a polycarboxylic acid anhydride) as the target product, reaction intermediate or reaction byproduct. The hydroxylamine can be free hydroxylamine as, for example, an aqueous solution of hydroxylamine, or a salt of hydroxylamine. The salt of hydroxylamine includes a hydrochloride, a sulfate, and a nitrate. A base is generally used when a hydroxylamine salt is used. Examples of the base are amines such as triethylamine; nitrogen-containing heterocyclic compounds such as pyridine; alkali metal alkoxides such as sodium methoxide and sodium ethoxide; organic acid salts of alkali metals, such as sodium acetate and potassium acetate; ammonia; alkali metal hydroxides such as sodium hydroxide and potassium hydroxide; alkali metal carbonates such as sodium carbonate; alkali metal hydrogen carbonates such as sodium hydrogen carbonate; and alkaline earth metal hydroxides such as magnesium hydroxide and calcium hydroxide.

The amount of hydroxylamine or a salt thereof is generally about 1 mole or more (for example, about 1 to about 10 moles), preferably about 1 to about 5 moles, and more preferably about 1 to about 3 moles, per 1 mole of the component to be treated, such as a polycarboxylic acid. The hydroxylamine can be used as a solvent. The reaction temperature is generally about 0° C. to about 150° C., and preferably about 5° C. to about 120° C. When a polycarboxylic acid is used, the reaction may be carried out while distilling off by-produced water. Alternatively or in addition, a scavenger for water (a dehydrating agent) may be added to the reaction system. The produced N-hydroxyimide compound can be separated and purified after the completion of the reaction by a conventional separation/purification operation (or device) such as filtration, concentration, extraction, crystallization, or recrystallization. The N-hydroxyimide compound can be subjected to the oxidation reaction as such a purified product or as a mixture with one or more other components, or may be subjected to the oxidation relation after a simple purification operation (or device).

The N-(substituted oxy)-imide compound such as a cyclic N-(substituted oxy)-imide compound can be produced from the produced N-hydroxyimide compound, such as a cyclic N-hydroxyimide compound, by a method according to the type of a substituent bound to the oxygen atom. For example, an N-acyloxyimide compound can be produced by reacting a N-hydroxyimide compound with an acid anhydride corresponding to the acyl group or with an acid halide corresponding to the acyl group in the presence of a base. More specifically, the N-acetoxyimide compound can be produced by reacting a N-hydroxyimide compound with acetic anhydride or with an acetyl halide such as acetyl chloride in the presence of a base such as triethylamine or pyridine. The produced N-(substituted oxy)-imide compound can be separated and purified after the completion of the reaction by a conventional separation/purification operation (or device) such as filtration, concentration, extraction, crystallization, or recrystallization. As the N-hydroxyimide compound, the N-(substituted oxy)-imide compound can be subjected to the oxidation reaction as such a purified product or as a mixture with one or more other components, or may be subjected to the oxidation relation after a simple purification operation (or device).

The N-(substituted oxy)-imide compound such as a cyclic N-(substituted oxy)-imide compound can also be produced by reacting a polycarboxylic acid or a polycarboxylic acid anhydride with a O-substituted hydroxylamine or a salt thereof. The N-hydroxyimide compound such as a cyclic N-hydroxyimide compound can also be obtained, for example, by subjecting the thus-produced N-(substituted oxy)-imide compound such as a cyclic N-(substituted oxy)-imide compound to hydrolysis to thereby replace the substituent bound to the oxygen atom with hydrogen atom.

The production of the catalyst within the oxidation reaction system (in situ) can be carried out, for example, by adding hydroxylamine to the oxidation reaction system.

As is described above, according to the present invention, a loss of the catalyst due to denaturation can be easily made up for by effectively using a target product, a reaction intermediate, and/or a reaction byproduct each formed as a result of the reaction.

The process for producing an organic compound according to the present invention is based on the oxidation method of an organic compound according to the present invention. The process for producing an organic compound according to the present invention comprises the steps of (A) oxidizing an organic compound with oxygen by the catalysis of at least one N-hydroxy- or N-(substituted oxy)-imide compound derivable from at least one selected from the group consisting of a target product, a reaction intermediate, and a reaction byproduct, (B) separating the target product formed in Step A from at least one component selected from the group consisting of a target product, reaction intermediate, and reaction byproduct each being formed as a result of the reaction and being to be used for producing the catalyst so as to make up for a loss of the catalyst due to denaturation in the reaction, (C) producing a catalyst using the at least one component separated in Step B, and (D) supplying the catalyst produced in Step C to Step A. The process may further comprise the step of (E) recovering an undenaturated catalyst from a reaction mixture and recycling the recovered undenaturated catalyst to Step A, in addition to those steps. FIG. 1 is a schematic process chart of an example of the production process according to the present invention.

In Reaction Step A, an organic compound (a substrate) fed from a line 1 is subjected to an oxidation reaction with oxygen in the presence of a catalyst N-hydroxy- or N-(substituted oxy)-imide compound derivable from a target compound, a reaction intermediate, and/or a reaction byproduct. A reaction apparatus for use in Reaction Step A can comprise, for example, a reactor for oxidizing the substrate; a supplying device for supplying the substrate, the catalyst, and an oxygen-containing gas to the reactor, such as a charging line, a charging pump, and a sparger; a mixing device for admixing the substrate, catalyst, and oxygen-containing gas, such as a stirrer; a device for adjusting the reaction temperature; and a discharging device for discharging a reaction mixture and/or a waste gas from the reactor.

In Separation Step B, the target product and at least one component selected from the group consisting of the target product, reaction intermediate, and reaction byproduct each formed as a result of the reaction (a component for the production of catalyst) are separated from the reaction mixture fed from Reaction Step A via a line 2, which component for the production of catalyst is to be used for producing the catalyst so as to make up for a loss of the catalyst due to denaturation in the reaction. The catalyst (undenaturated catalyst) may be contained in the component for the production of catalyst or may be separated from the component and returned via a line 5 to Reaction Step A (Catalyst Recycling Step E). The separation of the target product from the component for the production of catalyst can be conducted by a separation/purification operation such as filtration, concentration, distillation, extraction, crystallization, or recrystallization, or using a separation device such as a filtering device, a concentrator, a distillator, an extractor, a crystallizer or a recrystallizer. The separated target product is recovered via a line 3, is further purified according to necessity and thereby yields a final product. Part or all of the separated component for the production of catalyst is subjected to Catalyst Production Step C via a line 4, followed by the production of catalyst for make up for a denaturated catalyst. When part of the component for the production of catalyst is subjected to Catalyst Production Step C, the remainder or a necessary component thereof may be recycled to Reaction Step A or wasted. The mixture to be fed to Catalyst Production Step C via the line 4 may contain a denaturated product of the catalyst N-hydroxy- or N-(substituted oxy)-imide compound.

According to Catalyst Production Step C, the catalyst is produced using the component for the production of catalyst fed from Separation Step B via the line 4. An apparatus for producing the catalyst may comprise, for example, a reactor for reacting reaction components; a device for supplying the reaction components to the reactor, such as a charging line and/or a charging pump; a mixing device for admixing the reaction components, such as a stirrer; a device for adjusting the reaction temperature; a device for adjusting pH of the reaction system; a device for exhausting water by-produced in the reaction to outside the system, such as a water-separation device; a device for discharging the reaction mixture from the reactor; and/or a device for separating/purifying the produced catalyst.

According to Catalyst Supplying Step D, the catalyst produced in Catalyst Production Step C is supplied via a line 6 to Reaction Step A. According to Catalyst Recycling Step E, the catalyst separated and recovered in Separation Step B (undenaturated catalyst) is recycled via a line 5 to Reaction Step A. The supply of the produced catalyst to Reaction Step A, and the recycling of the undenaturated catalyst to Reaction Step A can be conducted according to a conventional procedure, such as a process of feeding these components to the reactor as intact or after dissolving or suspending them in a suitable solvent or medium. As a supplying device, a pump or a belt conveyer, for example, can be used. The operations in the steps may be carried out by any system such as a continuous system or batch system. Each step may use one or plural plies of apparatus or equipment, such as a reactor.

EXAMPLES

The present invention will be illustrated in further detail with reference to Examples below, which by no means limit the scope of the present invention.

Example 1

In a 2000-cc titanium autoclave were placed 450 g of cyclohexane, 550 g of acetic acid, 0.690 g of N-hydroxysuccinimide, and 9.960 g of cobalt acetate tetrahydrate, and the autoclave was pressurized to 3 MPa with a 50:50 (by mole) gaseous mixture of oxygen and nitrogen. The autoclave was held to 105° C. on an oil bath for carrying out a reaction for forty-five minutes, was cooled to room temperature, and opened to release the pressure. The resulting reaction mixture included a solid layer mainly containing adipic acid, and a liquid layer. The liquid layer contained two separated layers, i.e., an upper layer mainly containing cyclohexane, and a lower layer mainly containing acetic acid. Each of these layers was separated and analyzed to find that the conversion from cyclohexane was 17.3% and the selectivities of adipic acid, cyclohexanone, cyclohexanol, and succinic acid were 54.3%, 11.2%, 7.5%, and 4.2%, respectively.

Next, the lower layer of the liquid layer was concentrated at 140° C. and 100 Torr (13.3 kPa) using an evaporator and thereby yielded 48.1 g of a concentrate. The concentrate was washed with two portions of 40 g of acetic acid. The washed concentrate was 45.4 g in weight. This concentrate contained 10.1 percent by weight of succinic acid, 14.1 percent by weight of glutaric acid, and 72.9 percent by weight of adipic acid.

The concentrate was placed in a 300-ml flask and was combined with 30.2 g of acetic acid. The flask had been equipped with a Dean-Stark fractionating unit, a thermometer, and an agitating blade, and the Dean-Stark fractionating unit had a reflux condenser on an upper portion thereof. The flask was heated on an oil bath, and from the time when acetic acid began distilling, a 50 percent by weight aqueous hydroxylamine solution was fed to the flask at a rate of 0.39 g/hr, and the distillate was extracted at a rate of 11.33 g/hr while feeding acetic acid to the flask so as to keep the liquid level inside the flask. Eight hours later, the extraction of distillate, and supply of acetic acid and the aqueous hydroxylamine solution were stopped, and the flask was cooled. The resulting mixture (78.9 g) contained 4.37 g of N-hydroxysuccinimide and 0.24 g of N-hydroxyglutarimide.

An aliquot of this mixture (12.44 g) was diluted with 540 g of acetic acid, and placed together with 450 g of cyclohexane and 8.39 g of cobalt acetate tetrahydrate in a 2000-cc titanium autoclave, and the autoclave was pressurized to 3 MPa with a 50:50 (by mole) gaseous mixture of oxygen and nitrogen. The autoclave was held to 105° C. on an oil bath to carry out a reaction for forty-five minutes, cooled to room temperature, and opened to release the pressure. The resulting mixture contained a solid layer mainly containing adipic acid, and a liquid layer, as in the first reaction. The liquid layer had been separated into two layers, i.e., an upper layer mainly containing cyclohexane, and a lower layer mainly containing acetic acid. Each of these layers was separated and analyzed to find that the conversion from cyclohexane was 17.1%, and the selectivities of adipic acid, cyclohexanone, cyclohexanol, and succinic acid were 53.9%, 12.1%, 7.9%, and 4.6%, respectively.

Example 2

In a 500-cc titanium autoclave were placed 6.3 g of durene, 87.8 g of acetic acid, 1.165 g of N,N'-dihydroxypyromellitic diimide, 0.058 g of manganese acetate tetrahydrate, 0.234 g of cobalt acetate tetrahydrate, and 0.053 g of zirconium oxoacetate, and the autoclave was pressurized to 4 MPa with a 50:50 (by mole) gaseous mixture of oxygen and nitrogen. The autoclave was held to 120° C. on an oil bath to carry out a reaction for two hours, cooled to room temperature, and opened to release the pressure. The resulting mixture was combined with 29.2 g of acetic anhydride, and the autoclave was pressurized to 0.5 MPa with nitrogen. The autoclave was held to 120° C. on an oil bath to carry out a reaction for one hour, cooled to room temperature, and opened to release the pressure. The mixture was further combined with 1.165 g of N,N'-dihydroxypyromellitic diimide, and the autoclave was pressurized to 4 MPa with a 50:50 (by mole) gaseous mixture of oxygen and nitrogen. The autoclave was held to 150° C. on an oil bath to carry out a reaction for three hours, cooled to room temperature, and opened to release the pressure. The reaction mixture was analyzed by high-performance liquid chromatography (HPLC) to find that pyromellitic acid and pyromellitic anhydride were obtained in a total yield of 83%.

The mixture in the flask was filtrated to remove precipitates, the filtrate was placed in another flask, concentrated on an oil bath at 150° C., and thereby yielded 31.5 g of a concentrate. The crystals were washed with 5 cc of acetic acid and 5 cc of acetone, subjected to vacuum drying at 130° C. for twelve hours, and thereby yielded 7.27 g of crystals. The crystals were analyzed by NMR to find that they contained pyromellitic anhydride and pyromellitic acid in a molar ratio of the former to the latter of 100:7.

The crystals were then combined with a solution of 4.82 g of hydroxylamine hydrochloride and 46.6 g of pyridine, and heated at 80° C. for fifteen minutes. After cooling, the precipitate was filtrated and washed with 15 g of water. The crystals were combined with 20 g of a 32 percent by weight aqueous acetic acid solution and were stirred at room temperature for thirty minutes. The crystals were filtrated, washed with 7 g of a 9 percent by weight aqueous acetic acid solution, combined with 15 cc of acetone, and stirred at room temperature for two hours. The resulting crystals were filtrated, washed with 5 cc of acetone, dried at 45° C. for twelve hours, and thereby yielded 6.68 g of N,N'-dihydroxypyromellitic diimide.

An oxidation reaction of durene was conducted using the above-prepared N,N'-dihydroxypyromellitic diimide by the procedure as above, and the resulting reaction mixture was analyzed by HPLC to find that pyromellitic acid and pyromellitic anhydride were obtained in a total yield of 81%, which was substantially the same result as in the first reaction.

INDUSTRIAL APPLICABILITY

In regard to the method of oxidizing an organic compound with oxygen and the production process of an organic compound, in the course of oxidation of organic compounds with oxygen in the presence of a catalyst N-hydroxy- or N-(substituted oxy)-imide compound, losses of the catalysts due to denaturation can be easily, conveniently, and inexpensively made up.

The invention claimed is:

1. A method for oxidizing an organic compound with oxygen in the presence of a catalyst,
    wherein the catalyst comprises at least one N-hydroxy- or N-(substituted oxy)-imide compound derivable from at least one selected from the group consisting of a target product, reaction intermediate, and reaction byproduct, wherein the reaction intermediate or reaction byproduct is extracted as a mixture with one or more other components from a reaction mixture, and wherein the method comprises the steps of:
    producing the catalyst from at least one component selected from the group consisting of the target product, reaction intermediate, and reaction byproduct, wherein the reaction intermediate or reaction byproduct is extracted as a mixture with one or more other components from a reaction mixture, and
    each formed as a result of the reaction; and
    using the produced catalyst in the oxidation reaction so as to make up for a loss of the catalyst due to denaturation in the reaction,
    wherein the organic compound is at least one component selected from the group consisting of a cycloalkane represented by Formula (1) and a compound represented by following Formula (3), Formula (6) and Formula (9):

[Chemical Formula 1]

(1)

wherein "n" represents an integer of 5 to 15, and the ring shown in Chemical Formula (1) may have one or more substituents within ranges not adversely affecting the oxidation reaction, wherein the substituent is selected from the group consisting of halogen atoms, alkyl groups which may have one or more halogen atoms, cycloalkyl groups, aryl groups, alkoxy groups which may have one or more halogen atoms, protected or unprotected hydroxyl group, protected or unprotected hydroxy(halo)alkyl groups, protected or unprotected amino groups, protected or unprotected carboxyl group, protected or unprotected sulfo group, protected or unprotected acyl groups, cyano group, nitro group, and oxo group (=O),

[Chemical Formula 3]

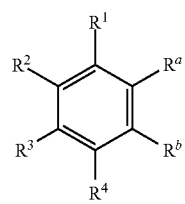

(3)

wherein $R^a$ and $R^b$ are the same as or different from each other and each represents an organic group having a carbon-hydrogen bond at the benzyl position of the aromatic ring; $R^1$, $R^2$, $R^3$, and $R^4$ are the same as or different from one another and each represents hydrogen atom, a halogen atom, or an organic group selected from the group consisting of alkyl groups which may have one or more halogen atoms, phenyl group, protected or unprotected hydroxyl group, and alkoxy groups which may have one or more halogen atoms, where two or more of $R^a$, $R^b$, $R^1$, $R^2$, $R^3$, and $R^4$ may be combined to form an aromatic or nonaromatic ring together with one or more carbon atoms constituting the benzene ring,

[Chemical Formula 6]

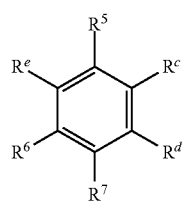

(6)

wherein $R^c$, $R^d$, and $R^e$ are the same as or different from one another and each represents an organic group having a carbon-hydrogen bond at the benzyl position of the aromatic ring; and $R^5$, $R^6$, and $R^7$ are the same as or different from one another and each represents hydrogen atom, a halogen atom, or an organic group selected from the group consisting of alkyl groups which may have one or more halogen atoms, phenyl group, protected or unprotected hydroxyl group, and alkoxy groups which may have one or more halogen atoms, and wherein two or more of $R^c$, $R^d$, $R^e$, $R^5$, $R^6$, and $R^7$ may be combined to form an aromatic or nonaromatic ring together with one or more carbon atoms constituting the benzene ring,

[Chemical Formula 9]

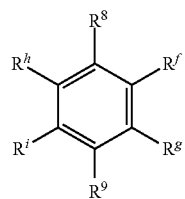

(9)

wherein $R^f$, $R^g$, $R^h$, and $R^i$ are the same as or different from one another and each represents an organic group having a carbon-hydrogen bond at the benzyl position of the aromatic ring; and $R^8$ and $R^9$ are the same as or different from each other and each represents hydrogen atom, a halogen atom, or an organic group selected from the group consisting of alkyl groups which may have one or more halogen atoms, phenyl group, protected or unprotected hydroxyl group, and alkoxy groups which may have one or more halogen atoms, where two or more of $R^f$, $R^g$, $R^h$, $R^i$, $R^8$, and $R^9$ may be combined to form a nonaromatic ring together with one or more carbon atoms constituting the benzene ring, and wherein the at least one component selected from the group consisting of the target product, reaction intermediate, and reaction byproduct is at least one selected from the group consisting of polycarboxylic acids, polycarboxylic acid anhydrides, and mixtures thereof, wherein the reaction intermediate or reaction byproduct is extracted as a mixture with one or more other components from a reaction mixture;

and wherein (I) when the organic compound is the cycloalkane represented by Formula (1), it is oxidized with oxygen to thereby yield at least one selected from the group consisting of a corresponding cycloalkanone, a corresponding cycloalkanol, and a corresponding dicarboxylic acid having carbon atoms in the number of "n" in principal chain, wherein the catalyst comprises at least one cyclic N-hydroxy- or N-(substituted oxy)-imide compound derivable from at least one selected from the group consisting of polycarboxylic acids, polycarboxylic acid anhydrides, and mixtures thereof formed as a result of the reaction and represented by following Formula (2):

[Chemical Formula 2]

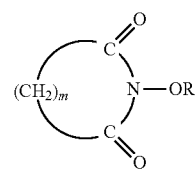

(2)

wherein "m" represents an integer of 2 to (n−2); and R represents hydrogen atom; groups that can form acetal or hemiacetal group with an adjacent oxygen atom; groups corresponding to an acid except that OH group is removed therefrom, and wherein the ring shown in the formula may have one or more substituents within ranges not adversely affecting the oxidation reaction, wherein the substituent is selected from the group consisting of halogen atoms, alkyl groups which may have one or more halogen atoms, cycloalkyl groups, aryl groups, alkoxy groups which may have one or more halogen atoms, protected or unprotected hydroxyl group, protected or unprotected hydroxy(halo)alkyl groups, protected or unprotected amino groups, protected or unprotected carboxyl group, protected or unprotected sulfo group, protected or unprotected acyl groups, cyano group, nitro group, and oxo group (═O), and wherein the method comprises the steps of:
producing the catalyst from at least one component selected from the group consisting of polycarboxylic acids, polycarboxylic acid anhydrides, and mixtures thereof formed as a result of the reaction; and using the produced catalyst in the oxidation reaction so as to make up for a loss of the catalyst due to denaturation in the reaction;
and wherein
(II) when the organic compound is the compound represented by Formula (3), it is oxidized with oxygen to thereby yield at least one selected from the group consisting of an aromatic dicarboxylic acid represented by following Formula (4a) and an aromatic dicarboxylic acid anhydride represented by following Formula (4b):

[Chemical Formula 4]

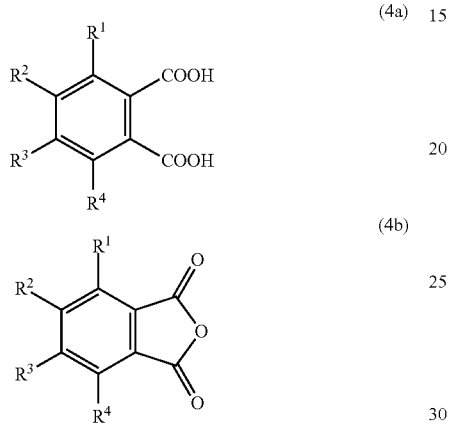

(4a)

(4b)

wherein $R^1$, $R^2$, $R^3$, and $R^4$ are the same as or different from one another and each represents hydrogen atom, a halogen atom, or an organic group selected from the group consisting of alkyl groups which may have one or more halogen atoms, phenyl group, protected or unprotected hydroxyl group, and alkoxy groups which may have one or more halogen atoms, where two or more of $R^1$, $R^2$, $R^3$, and $R^4$ may be combined to form an aromatic or non-aromatic ring together with one or more carbon atoms constituting the benzene ring,
wherein the catalyst comprises at least one cyclic imide compound derivable from at least one selected from the group consisting of polycarboxylic acids, polycarboxylic acid anhydrides, and mixtures thereof formed as a result of the reaction and represented by following Formula (5):

[Chemical Formula 5]

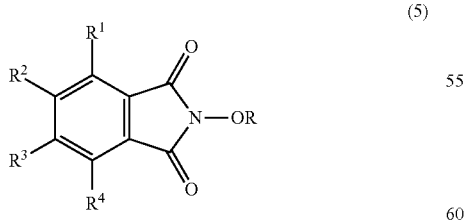

(5)

wherein $R^1$, $R^2$, $R^3$, and $R^4$ are the same as or different from one another and each represents hydrogen atom, a halogen atom, or an organic group selected from the groups consisting of alkyl groups which may have one or more halogen atoms, phenyl group, protected or unprotected hydroxyl group, and alkoxy groups which may have one or more halogen atoms, where two or more of $R^1$, $R^2$, $R^3$, and $R^4$ may be combined to form an aromatic or non-aromatic ring together with one or more carbon atoms constituting the benzene ring; and R represents hydrogen atom; groups that can form acetal or hemiacetal group with an adjacent oxygen atom; groups corresponding to an acid except that OH group is removed therefrom, and
wherein the method comprises the steps of:
producing the catalyst from at least one component selected from the group consisting of polycarboxylic acids, polycarboxylic acid anhydrides, and mixtures thereof formed as a result of the reaction; and
using the produced catalyst in the oxidation reaction so as to make up for a loss of the catalyst due to denaturation in the reaction;
and wherein
(III) when the organic compound is the compound represented by Formula (6), it is oxidized with oxygen to thereby yield at least one of an aromatic tricarboxylic acid represented by following Formula (7a) and an aromatic tricarboxylic acid monoanhydride represented by following Formula (7b):

[Chemical Formula 7]

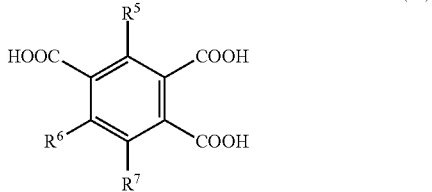

(7a)

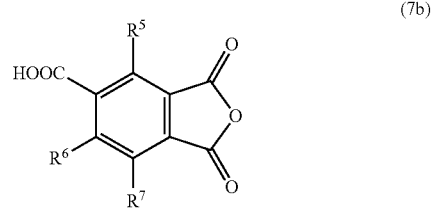

(7b)

wherein $R^5$, $R^6$, and $R^7$ are the same as or different from one another and each represents hydrogen atom, a halogen atom, or an organic group selected from the group consisting of alkyl groups which may have one or more halogen atoms, phenyl group, protected or unprotected hydroxyl group, and alkoxy groups which may have one or more halogen atoms, where two or more of $R^5$, $R^6$, and $R^7$ may be combined to form an aromatic or non-aromatic ring together with one or more carbon atoms constituting the benzene ring,
wherein the catalyst comprises at least one cyclic imide compound derivable from at least one selected from the group consisting of polycarboxylic acids, polycarboxylic acid anhydrides, and mixtures thereof formed as a result of the reaction and represented by following Formula (8):

[Chemical Formula 8]

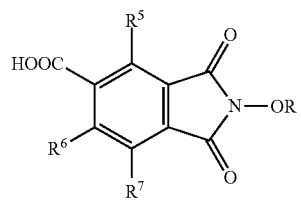

(8)

wherein $R^5$, $R^6$, and $R^7$ are the same as or different from one another and each represents hydrogen atom, a halogen atom, or an organic group selected from the group consisting of alkyl groups which may have one or more halogen atoms, phenyl group, protected or unprotected hydroxyl group, and alkoxy groups which may have one or more halogen atoms, where two or more of $R^5$, $R^6$, and $R^7$ may be combined to form an aromatic or non-aromatic ring together with one or more carbon atoms constituting the benzene ring; and R represents hydrogen atom; groups that can form acetal or hemiacetal group with an adjacent oxygen atom; groups corresponding to an acid except that OH group is removed therefrom, and wherein the method comprises the steps of:

producing the catalyst from at least one component selected from the group consisting of polycarboxylic acids, polycarboxylic acid anhydrides, and mixtures thereof formed as a result of the reaction; and using the produced catalyst in the oxidation reaction so as make up for a loss of the catalyst due to denaturation in the reaction;

and wherein (IV) when the organic compound is the compound represented by Formula (9), it is oxidized with oxygen to thereby yield at least one selected from the group consisting of an aromatic tetracarboxylic acid represented by following Formula (10a), an aromatic tetracarboxylic acid monoanhydride represented by following Formula (10b), and an aromatic tetracarboxylic acid dianhydride represented by following Formula (10c):

[Chemical Formula 10]

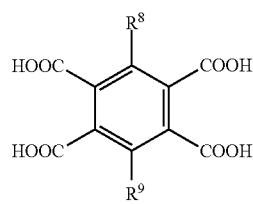

(10a)

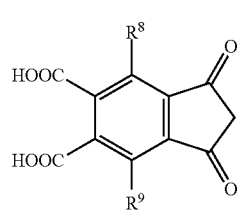

(10b)

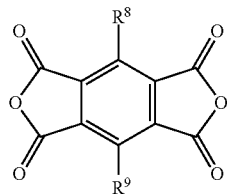

(10c)

wherein $R^8$ and $R^9$ are the same as or different from each other and each represents hydrogen atom, a halogen atom, or an organic group selected from the group consisting of alkyl groups which may have one or more halogen atoms, phenyl group, protected or unprotected hydroxyl group, and alkoxy groups which may have one or more halogen atoms, wherein the catalyst comprises at least one of a cyclic imide compound represented by following Formula (11a) and a cyclic diimide compound represented by following Formula (11b), each being derivable from at least one selected from the group consisting of polycarboxylic acids, polycarboxylic acid anhydrides, and mixtures thereof formed as a result of the reaction:

[Chemical Formula 11]

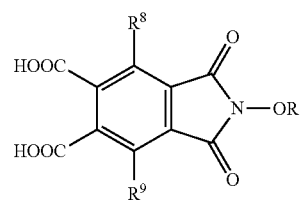

(11a)

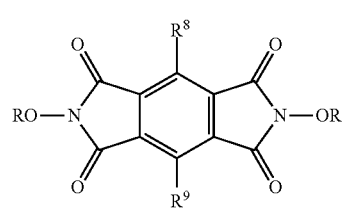

(11b)

wherein $R^8$ and $R^9$ are the same as or different from each other and each represents hydrogen atom, a halogen atom, or an organic group selected from the group consisting of alkyl groups which may have one or more halogen atoms, phenyl group, protected or unprotected hydroxyl group, and alkoxy groups which may have one or more halogen atoms; and R represents hydrogen atom; groups that can form acetal or hemiacetal group with an adjacent oxygen atom; groups corresponding to an acid except that OH group is removed therefrom, and wherein the method comprises the steps of:

producing the catalyst from at least one component selected from the group consisting of polycarboxylic acids, polycarboxylic acid anhydrides, and mixtures thereof formed as a result of the reaction; and using the produced catalyst in the oxidation reaction so as make up for a loss of the catalyst due to denaturation in the reaction.

2. The method of claim 1, wherein the at least one N-hydroxy- or N-(substituted oxy)-imide compound is a cyclic N-hydroxy- or N-(substituted oxy)-imide compound.

3. The method of one of claims 1 and 2, further comprising the steps of:
recovering an undenatured catalyst from a reaction mixture; and
using the recovered undenatured catalyst in the oxidation reaction, in addition to the catalyst produced from at least one component selected from the group consisting of polycarboxylic acids, polycarboxylic acid anhydrides, and mixtures thereof, each formed as a result of the reaction.

4. The method of claim 1, for oxidizing cyclohexane with oxygen to thereby yield at least one selected from the group consisting of cyclohexanone, cyclohexanol, and adipic acid,
wherein the catalyst comprises at least one selected from the group consisting of N-hydroxy- or N-(substituted oxy)-succinimide and N-hydroxy- or N-(substituted oxy)-glutarimide derived from succinic acid and glutaric acid, respectively, each as a reaction byproduct, and
wherein the method comprises the steps of:
producing the catalyst from succinic acid and/or glutaric acid formed as a result of the reaction; and
using the produced catalyst in the oxidation reaction so as make up for a loss of the catalyst due to denaturation in the reaction.

5. The method of claim 1, for oxidizing cyclopentane with oxygen to thereby yield at least one selected from the group consisting of cyclopentanone, cyclopentanol, and glutaric acid,
wherein the catalyst comprises at least one selected from the group consisting of N-hydroxy- or N-(substituted oxy)-succinimide derived from succinic acid as a reaction byproduct, and N-hydroxy- or N-(substituted oxy)-glutarimide derived from glutaric acid as a target product, and
wherein the method comprises the steps of:
producing the catalyst from succinic acid and/or glutaric acid formed as a result of the reaction; and
using the produced catalyst in the oxidation reaction so as make up for a loss of the catalyst due to denaturation in the reaction.

6. The method of claim 1, for oxidizing cyclododecane with oxygen to thereby yield at least one selected from the group consisting of cyclododecanone, cyclododecanol, and dodecanedioic acid,
wherein the catalyst comprises at least one selected from the group consisting of N-hydroxy- or N-(substituted oxy)-succinimide, and N-hydroxy- or N-(substituted oxy)-glutarimide derived from succinic acid and glutaric acid, respectively, as reaction byproducts, and
wherein the method comprises the steps of:
producing the catalyst from succinic acid and/or glutaric acid formed as a result of the reaction; and
using the produced catalyst in the oxidation reaction so as make up for a loss of the catalyst due to denaturation in the reaction.

7. The method of claim 1, further comprising the steps of:
producing the catalyst from at least one component selected from the group consisting of the aromatic dicarboxylic acid represented by Formula (4a) and the aromatic dicarboxylic acid anhydride represented by Formula (4b) each formed as a result of the reaction; and
using the produced catalyst in the oxidation reaction.

8. The method of claim 1, further comprising the steps of:
producing the catalyst from at least one component selected from the group consisting of an aromatic tricarboxylic acid represented by Formula (7a) and an aromatic tricarboxylic acid monoanhydride represented by Formula (7b) each formed as a result of the reaction; and
using the produced catalyst in the oxidation reaction.

9. The method of claim 1, further comprising the steps of:
producing the catalyst from at least one component selected from the group consisting of the aromatic tetracarboxylic acid represented by Formula (10a), the aromatic tetracarboxylic acid monoanhydride represented by Formula (10b), and the aromatic tetracarboxylic acid dianhydride represented by Formula (10c), each formed as a result of the reaction; and
using the produced catalyst in the oxidation reaction.

10. A process for producing an organic compound, comprising the steps of:
(A) oxidizing an organic compound with oxygen by a catalyst of at least one N-hydroxy- or N-(substituted oxy)-imide compound derivable from at least one selected from the group consisting of a target product, a reaction intermediate, and a reaction byproduct wherein the reaction intermediate or reaction byproduct is extracted as a mixture with one or more other components from a reaction mixture;
wherein the organic compound is at least one component selected from the group consisting of a cycloalkane represented by following Formula (1) and a compound represented by following Formula (3), Formula (6) and Formula (9):

[Chemical Formula 1]

(1)

wherein "n" represents an integer of 5 to 15, and the ring shown in the formula may have one or more substituents within ranges not adversely affecting the oxidation reaction, wherein the substituent is selected from the group consisting of halogen atoms, alkyl groups which may have one or more halogen atoms, cycloalkyl groups, aryl groups, alkoxy groups which may have one or more halogen atoms, protected or unprotected hydroxyl group, protected or unprotected hydroxy(halo)alkyl groups, protected or unprotected amino groups, protected or unprotected carboxyl group, protected or unprotected sulfo group, protected or unprotected acyl groups, cyano group, nitro group, and oxo group (=O),

[Chemical Formula 3]

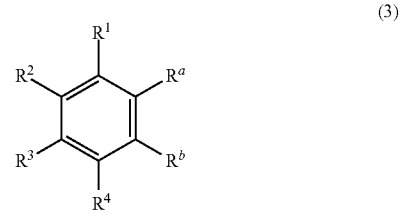

(3)

wherein $R^a$ and $R^b$ are the same as or different from each other and each represents an organic group having a carbon-hydrogen bond at the benzyl position of the aromatic ring; $R^1$, $R^2$, $R^3$, and $R^4$ are the same as or different from one another and each represent hydrogen atom, a halogen atom, or an organic group selected from the group consisting of alkyl groups which may have one or more halogen atoms, phenyl group, protected or unprotected hydroxyl group, and alkoxy groups which may have one or more halogen atoms, where two or more of $R^a$, $R^b$, $R^1$, $R^2$, $R^3$, and $R^4$ may be combined to form an aromatic or nonaromatic ring together with one or more carbon atoms constituting the benzene ring,

[Chemical Formula 6]

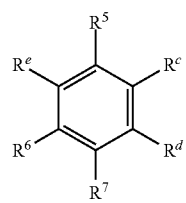

(6)

wherein $R^c$, $R^d$, and $R^e$ are the same as or different from one another and each represents an organic group having a carbon-hydrogen bond at the benzyl position of the aromatic ring; and $R^5$, $R^6$, and $R^7$ are the same as or different from one another and each represent hydrogen atom, a halogen atom, or an organic group selected from the group consisting of alkyl groups which may have one or more halogen atoms, phenyl group, protected or unprotected hydroxyl group, and alkoxy groups which may have one or more halogen atoms, where two or more of $R^c$, $R^d$, $R^e$, $R^5$, $R^6$, and $R^7$ may be combined to form an aromatic or nonaromatic ring together with one or more carbon atoms constituting the benzene ring,

[Chemical Formula 9]

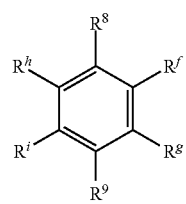

(9)

wherein $R^f$, $R^g$, $R^h$, and $R^i$ are the same as or different from one another and each represents an organic group having a carbon-hydrogen bond at the benzyl position of the aromatic ring; and $R^8$ and $R^9$ are the same as or different from each other and each represents hydrogen atom, a halogen atom, or an organic group selected from the group consisting of alkyl groups which may have one or more halogen atoms, phenyl group, protected or unprotected hydroxyl group, and alkoxy groups which may have one or more halogen atoms, where two or more of $R^f$, $R^g$, $R^h$, $R^i$, $R^8$, and $R^9$ may be combined to form a nonaromatic ring together with one or more carbon atoms constituting the benzene ring, and wherein the at least one component selected from the group consisting of the target product, reaction intermediate, and reaction byproduct is at least one selected from the group consisting of polycarboxylic acids, polycarboxylic acid anhydrides, and mixtures thereof, and wherein the reaction intermediate or reaction byproduct is extracted as a mixture with one or more other components from a reaction mixture;

(B) separating the target product formed in Step A from at least one component selected from the group consisting of a target product, reaction intermediate, and reaction byproduct, wherein the reaction intermediate or reaction byproduct is extracted as a mixture with one or more other components from a reaction mixture, each being formed as a result of the reaction and being to be used for producing the catalyst so as to make up for a loss of the catalyst due to denaturation in the reaction, wherein the at least one component selected from the group consisting of the target product, reaction intermediate, and reaction byproduct is at least one selected from the group consisting of polycarboxylic acids, polycarboxylic acid anhydrides, and mixtures thereof, and wherein the reaction intermediate or reaction byproduct is extracted as a mixture with one or more other components from a reaction mixture;

(C) producing the catalyst using the at least one component separated in Step B; and (D) supplying the catalyst produced in Step C to Step A and wherein (I) when the organic compound is the cycloalkane represented by Formula (1), it is oxidized with oxygen to thereby yield at least one selected from the group consisting of a corresponding cycloalkanone, a corresponding cycloalkanol, and a corresponding dicarboxylic acid having carbon atoms in the number of "n" in principal chain, wherein the catalyst comprises at least one cyclic N-hydroxy- or N-(substituted oxy)-imide compound derivable from at least one selected from the group consisting of polycarboxylic acids, polycarboxylic acid anhydrides, and mixtures thereof formed as a result of the reaction and represented by following Formula (2):

[Chemical Formula 2]

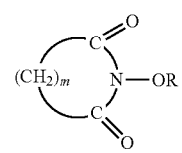

(2)

wherein "m" represents an integer of 2 to (n−2); and R represents hydrogen atom; groups that can form acetal or hemiacetal group with an adjacent oxygen atom; groups corresponding to an acid except that OH group is removed therefrom, and wherein the ring shown in the formula may have one or more substituents within ranges not adversely affecting the oxidation reaction, wherein the substituent is selected from the group consisting of halogen atoms, alkyl groups which may have one or more halogen atoms, cycloalkyl groups, aryl groups, alkoxy groups which may have one or more halogen atoms, protected or unprotected hydroxyl group, protected or unprotected hydroxy(halo)alkyl groups, protected or unprotected amino groups, protected or unprotected carboxyl group, protected or unprotected sulfo group, protected or unprotected acyl groups, cyano group, nitro group, and oxo group (=O), and wherein the method comprises the steps of:
producing the catalyst from at least one component selected from the group consisting of polycarboxylic acids, polycarboxylic acid anhydrides, and mixtures thereof formed as a result of the reaction; and using the produced catalyst in the oxidation reaction so as to make up for a loss of the catalyst due to denaturation in the reaction;

and wherein (II) when the organic compound is the compound represented by Formula (3), it is oxidized with oxygen to thereby yield at least one selected from the group consisting of an aromatic dicarboxylic acid represented by following Formula (4a) and an aromatic dicarboxylic acid anhydride represented by following Formula (4b):

[Chemical Formula 4]

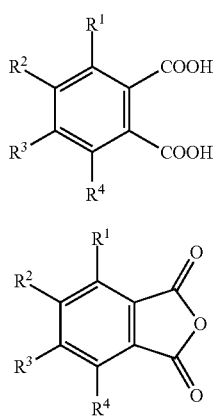

(4a)

(4b)

wherein $R^1$, $R^2$, $R^3$, and $R^4$ are the same as or different from one another and each represents hydrogen atom, a halogen atom, or an organic group selected from the group consisting of alkyl groups which may have one or more halogen atoms, phenyl group, protected or unprotected hydroxyl group, and alkoxy groups which may have one or more halogen atoms, where two or more of $R^1$, $R^2$, $R^3$, and $R^4$ may be combined to form an aromatic or non-aromatic ring together with one or more carbon atoms constituting the benzene ring, wherein the catalyst comprises at least one cyclic imide compound derivable from at least one selected from the group consisting of polycarboxylic acids, polycarboxylic acid anhydrides, and mixtures thereof formed as a result of the reaction and represented by following Formula (5):

[Chemical Formula 5]

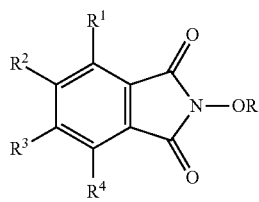

(5)

wherein $R^1$, $R^2$, $R^3$, and $R^4$ are the same as or different from one another and each represents hydrogen atom, a halogen atom, or an organic group selected from the groups consisting of alkyl groups which may have one or more halogen atoms, phenyl group, protected or unprotected hydroxyl group, and alkoxy groups which may have one or more halogen atoms, where two or more of $R^1$, $R^2$, $R^3$, and $R^4$ may be combined to form an aromatic or non-aromatic ring together with one or more carbon atoms constituting the benzene ring; and R represents hydrogen atom; groups that can form acetal or hemiacetal group with an adjacent oxygen atom; groups corresponding to an acid except that OH group is removed therefrom, and wherein the method comprises the steps of:

producing the catalyst from at least one component selected from the group consisting of polycarboxylic acids, polycarboxylic acid anhydrides, and mixtures thereof formed as a result of the reaction; and using the produced catalyst in the oxidation reaction so as to make up for a loss of the catalyst due to denaturation in the reaction;

and wherein (III) when the organic compound is the compound represented by Formula (6), it is oxidized with oxygen to thereby yield at least one of an aromatic tricarboxylic acid represented by following Formula (7a) and an aromatic tricarboxylic acid monoanhydride represented by following Formula (7b):

[Chemical Formula 7]

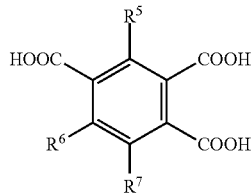

(7a)

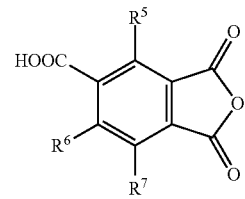

(7b)

wherein $R^5$, $R^6$, and $R^7$ are the same as or different from one another and each represents hydrogen atom, a halogen atom, or an organic group selected from the group consisting of alkyl groups which may have one or more halogen atoms, phenyl group, protected or unprotected hydroxyl group, and alkoxy groups which may have one or more halogen atoms, where two or more of $R^5$, $R^6$, and $R^7$ may be combined to form an aromatic or non-aromatic ring together with one or more carbon atoms constituting the benzene ring, wherein the catalyst comprises at least one cyclic imide compound derivable from at least one selected from the group consisting of polycarboxylic acids, polycarboxylic acid anhydrides, and mixtures thereof formed as a result of the reaction and represented by following Formula (8):

[Chemical Formula 8]

(8)

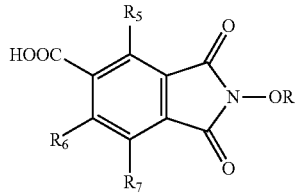

wherein $R^5$, $R^6$, and $R^7$ are the same as or different from one another and each represents hydrogen atom, a halogen atom, or an organic group selected from the group consisting of alkyl groups which may have one or more halogen atoms, phenyl group, protected or unprotected hydroxyl group, and alkoxy groups which may have one or more halogen atoms, where two or more of $R^5$, $R^6$, and $R^7$ may be combined to form an aromatic or non-aromatic ring together with one or more carbon atoms constituting the benzene ring; and R represents hydrogen atom; groups that can form acetal or hemiacetal group with an adjacent oxygen atom; groups corresponding to an acid except that OH group is removed therefrom, and wherein the method comprises the steps of:

producing the catalyst from at least one component selected from the group consisting of polycarboxylic acids, polycarboxylic acid anhydrides, and mixtures thereof formed as a result of the reaction; and using the produced catalyst in the oxidation reaction so as make up for a loss of the catalyst due to denaturation in the reaction;

and wherein (IV) when the organic compound is the compound represented by Formula (9), it is oxidized with oxygen to thereby yield at least one selected from the group consisting of an aromatic tetracarboxylic acid represented by following Formula (10a), an aromatic tetracarboxylic acid monoanhydride represented by following Formula (10b), and an aromatic tetracarboxylic acid dianhydride represented by following Formula (10c):

[Chemical Formula 10]

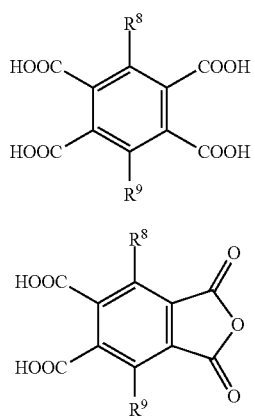

(10c)

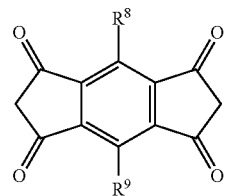

wherein $R^8$ and $R^9$ are the same as or different from each other and each represents hydrogen atom, a halogen atom, or an organic group selected from the group consisting of alkyl groups which may have one or more halogen atoms, phenyl group, protected or unprotected hydroxyl group, and alkoxy groups which may have one or more halogen atoms, wherein the catalyst comprises at least one of a cyclic imide compound represented by following Formula (11a) and a cyclic diimide compound represented by following Formula (11b), each being derivable from at least one selected from the group consisting of polycarboxylic acids, polycarboxylic acid anhydrides, and mixtures thereof formed as a result of the reaction:

[Chemical Formula 11]

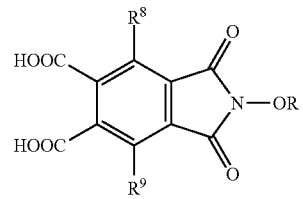

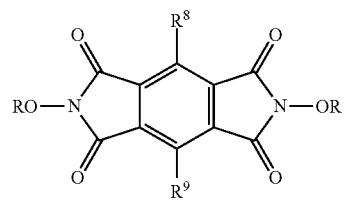

wherein $R^8$ and $R^9$ are the same as or different from each other and each represent hydrogen atom, a halogen atom, or an organic group selected from the group consisting of alkyl groups which may have one or more halogen atoms, phenyl group, protected or unprotected hydroxyl group, and alkoxy groups which may have one or more halogen atoms; and R represents hydrogen atom; groups that can form acetal or hemiacetal group with an adjacent oxygen atom; groups corresponding to an acid except that OH group is removed therefrom, and wherein the method comprises the steps of:

producing the catalyst from at least one component selected from the group consisting of polycarboxylic acids, polycarboxylic acid anhydrides, and mixtures thereof formed as a result of the reaction; and using the produced catalyst in the oxidation reaction so as make up for a loss of the catalyst due to denaturation in the reaction.

11. The process of claim 10, further comprising the step of (E) recovering an undenaturated catalyst from a reaction mixture and recycling the recovered undenaturated catalyst to Step A.

12. The method of claim 1,
wherein the ring shown in the Formula (1) has no substituent on the cycloalkane ring, and
wherein the ring shown in the Formula (2) has no substituent on the cycloalkane ring.

13. The method of claim 1, wherein R is selected from hydrogen atom and the group consisting of acyl groups, sulfonyl groups, alkoxycarbonyl groups, and carbamoyl groups.

* * * * *

UNITED STATES PATENT AND TRADEMARK OFFICE
CERTIFICATE OF CORRECTION

| | | |
|---|---|---|
| PATENT NO. | : 7,910,749 B2 | Page 1 of 1 |
| APPLICATION NO. | : 11/884203 | |
| DATED | : March 22, 2011 | |
| INVENTOR(S) | : Yasuteru Kajikawa et al. | |

It is certified that error appears in the above-identified patent and that said Letters Patent is hereby corrected as shown below:

On the Title Page:
Item (73) Assignee should read: Diacel Chemical Industries, Ltd., Sakai-shi, Osaka, (JP)

Signed and Sealed this
Eighteenth Day of October, 2011

David J. Kappos
*Director of the United States Patent and Trademark Office*

UNITED STATES PATENT AND TRADEMARK OFFICE
CERTIFICATE OF CORRECTION

Page 1 of 1

PATENT NO. : 7,910,749 B2
APPLICATION NO. : 11/884203
DATED : March 22, 2011
INVENTOR(S) : Yasuteru Kajikawa et al.

It is certified that error appears in the above-identified patent and that said Letters Patent is hereby corrected as shown below:

On the Title Page:
Item (73) Assignee should read: Daicel Chemical Industries, Ltd., Sakai-shi, Osaka, (JP)

This certificate supersedes the Certificate of Correction issued October 18, 2011.

Signed and Sealed this
Third Day of January, 2012

David J. Kappos
*Director of the United States Patent and Trademark Office*